US011034735B2

(12) United States Patent
Chudzinski-Tavassi et al.

(10) Patent No.: US 11,034,735 B2
(45) Date of Patent: Jun. 15, 2021

(54) HYBRID PEPTIDE, SET OF HYBRID PEPTIDES, COMPOSITION, USES OF THE HYBRID PEPTIDE, METHOD FOR INDUCING AN IMMUNE RESPONSE AND KITS

(71) Applicants: BIOTICK PESQUISA E DESENVOLVIMENTO TECNOLÓGICO LTDA., São Caetano do Sul-SP (BR); FUNDAÇÃO BUTANTAN, São Paulo-SP (BR)

(72) Inventors: Ana Marisa Chudzinski-Tavassi, São Paulo-SP (BR); Bárbara Athayde Vaz Galvão da Silva, São Paulo-SP (BR); Kerly Fernanda Mesquita Pasqualoto, São Paulo-SP (BR); Leo Kei Iwai, São Paulo-SP (BR); Rafael Marques Porto, São Paulo-SP (BR)

(73) Assignees: BIOTICK PESQUISA E DESENVOLVIMENTO TECNOLÓGICO LTDA., Caetano do Sul-SP (BR); FUNDAÇÃO BUTANTAN, São Paulo-SP (BR)

( * ) Notice: Subject to any disclaimer, the term of this patent is extended or adjusted under 35 U.S.C. 154(b) by 0 days.

(21) Appl. No.: 16/485,035

(22) PCT Filed: Feb. 9, 2018

(86) PCT No.: PCT/BR2018/050024
§ 371 (c)(1),
(2) Date: Aug. 9, 2019

(87) PCT Pub. No.: WO2018/145182
PCT Pub. Date: Aug. 16, 2018

(65) Prior Publication Data
US 2020/0095289 A1 Mar. 26, 2020

(30) Foreign Application Priority Data
Feb. 9, 2017 (BR) .......................... 102017002668-0

(51) Int. Cl.
C07K 14/29 (2006.01)
A61P 31/04 (2006.01)
A61K 39/02 (2006.01)
A61K 39/00 (2006.01)

(52) U.S. Cl.
CPC .......... *C07K 14/29* (2013.01); *A61K 39/0233* (2013.01); *A61P 31/04* (2018.01); *A61K 2039/552* (2013.01); *A61K 2039/55566* (2013.01); *A61K 2039/70* (2013.01); *C07K 2319/00* (2013.01)

(58) Field of Classification Search
None
See application file for complete search history.

(56) References Cited

U.S. PATENT DOCUMENTS

| | | |
|---|---|---|
| 3,511,908 A | 5/1970 | Brock et al. |
| 3,674,860 A | 7/1972 | Welter et al. |
| 4,956,278 A | 9/1990 | Hart et al. |
| 6,979,451 B1 | 12/2005 | de la Fuente et al. |
| 2005/0249749 A1 | 11/2005 | de La Fuente et al. |
| 2006/0194267 A1 | 8/2006 | Vojdani |
| 2007/0286871 A1 | 12/2007 | Hickle et al. |
| 2011/0143377 A1 | 6/2011 | Hoey et al. |
| 2015/0204868 A1 | 7/2015 | Mehra et al. |

FOREIGN PATENT DOCUMENTS

| | | |
|---|---|---|
| WO | 2015116907 | 8/2015 |
| WO | 2016205434 | 12/2016 |

OTHER PUBLICATIONS

International Search Report and Written Opinion in corresponding PCT/BR2018/050024, dated Apr. 6, 2018.
MacMillan, et al., "Physical Linkage of Naturally Complexed Bacterial Outer Membrane Proteins Enhances Immunogenicity", Infection and Immunity, Mar. 2008, p. 1223-1229.
Contreras, et al., "Bacterial membranes enhance the immunogenicity and protective capacity of the surface exposed tick Subolesin-Anaplasma marginale MSP1a chimeric antigen", Ticks Tick Borne Dis., Sep. 2015, 6(6), p. 820-828 (absract attached)
Canales, et al., "Anaplasma marginale major surface protein 1a directs cell surface display of tick BM95 immunogenic peptides on *Escherichia coli*", J Biotechnol., Jul. 31, 2008, 135(4), p. 326-332 (abstract attached).
Torina, et al., "Control of tick infestations and pathogen prevalence in cattle and sheep farms vaccinated with the recombinant Subolesin-Major Surface Protein 1a chimeric antigen", Parasit Vectors, Jan. 8, 2014, 7:10.
Cangussu, et al., "A hybrid protein containing MSP1a repeats and Omp7, Omp8 and Omp9 epitopes protect mmunized BALB/c mice against anaplasmosis", Vet Res (2018) 49:6.
Almazán, et al., "Control of tick infestations in cattle vaccinated with bacterial membranes containing surface-exposed tick protective antigens", Vaccine 30 (2012) 265-272.

(Continued)

*Primary Examiner* — Robert A Zeman
(74) *Attorney, Agent, or Firm* — Hovey Williams LLP

(57) ABSTRACT

The present invention relates to novel hybrid peptides developed from the combination of membrane surface protein peptide fragments present in anaplasmosis microorganisms, and in particular, bacteria of the species *Anaplasma marginale*. The present invention further relates to hybrid peptide sets, compositions and kits comprising such novel hybrid peptides, their uses and methods of inducing immune response. Each hybrid peptide, according to the present invention, comprises two or more peptide fragments of amino acid sequences as defined in the present invention linked together by means of a spacer element. The combined peptide fragments are protein peptide fragments of MSP1, MSP1a, MSP1b, MSP2, MSP2-HRV, MSP3, OMP7, OMP8, VirB9 and VirB10.

13 Claims, No Drawings
Specification includes a Sequence Listing.

(56) References Cited

OTHER PUBLICATIONS

McGuire, et al., "Recombinant vaccinia virus expression of Anaplasma marginale surface protein MSP-la: effect of promoters, leader sequences and GPI anchor sequence on antibody response", Vaccine 12 (1994) 465-471.
Brown, et al., "CD4+T Lymphocytes from Calves Immunized with Anaplasma marginale Major Surface Protein 1 (MSP1), a Heteromeric Complex of MSP1a and MSP1b, Preferentially Recognize the MSP1a Carboxyl Terminus That Is Conserved among Strains", Infection and Immunity 69 (2001) (11) 6853-6862.
Morse, et al., "Association and Evidence for Linked Recognition of Type IV Secretion System Proteins VirB9-1, VirB9-2, and VirB10 in Anaplasma marginale", Infection and Immunity 80 (2012) (1) 215-227.
Abbott, et al., "Rapid and long-term disappearance of CD4+ T lymphocyte responses specific for Anaplasma marginale major surface protein 2 (MSP2) in MSP2 vaccinates following challenge with live A. marginale", Journal of Immunology, 174 (2005) (11) 6702-6715.
Abbott, et al., "Anaplasma marginale major surface protein 2 CD4+-T-cell epitopes are evenly distributed in conserved and hypervariable regions (HVR), whereas linear B-cell epitopes are predominantly located in the HVR", Infection and Immunity, 75 (2004) (12) 7360-7366.
Agnes, et al., "Identification of Anaplasma marginale Outer Membrane Protein Antigens Conserved between A. marginale Sensu Stricto Strains and the Live A. marginale subsp. centrale Vaccine", Infection and Immunity, 79 (2011) (3) 1311-1318.
Araújo, et al., "IgG and IgG2 antibodies from cattle naturally infected with Anaplasma marginale recognize the recombinant vaccine candidate antigens VirB9, VirB10, and elongation factor-Tu", Mem. Inst. Oswaldo Cruz, 103 (2008) (2) 186-190.
Brown, et al., "The Hypervariable Region of Anaplasma marginale Major Surface Protein 2 (MSP2) Contains Multiple Immunodominant CD4 + T Lymphocyte Epitopes That Elicit Variant-Specific Proliferative and IFN- Responses in MSP2 Vaccinates", J Immunol, 170 (2003) 3790-3798.
Brown, et al., "CD4+ T Lymphocytes from Anaplasma marginale Major Surface Protein 2 (MSP2) Vaccinees Recognize Naturally Processed Epitopes Conserved in MSP3", Infection and Immunity, 72 (2004) (6) 3688-3692.
Crosby, et al., "Reduced Infectivity for Cattle of an Outer Membrane Protein mutant of Anaplasma marginale", Applied and Environmental Microbiology, 81 (2015) (6) 2206-2214.
Garcia-Garcia, et al., "Mapping of B-cell epitopes in the N-terminal repeated peptides of Anaplasma marginale major surface protein 1a and characterization of the humoral immune response of cattle immunized with recombinant and whole organism antigens", Veterinary Immunology and Immunopathology, 98 (2004) 137-151.
Gentilucci, et al., "Chemical Modifications Designed to Improve Peptide Stability: Incorporation of Non-Natural Amino Acids, Pseudo-Peptide Bonds, and Cyclization", Current Pharmaceutical Design, 16 (2010) 3185-3203.
Hammac, et al., "Protective immunity induced by immunization with a live, cultured Anaplasma marginale strain", Vaccine, 31 (2013) (35) 3617-3622.
Junior, et al., "Analysis of membrane protein genes in a Brazilian isolate of Anaplasma marginale", Memórias do Instituto Oswaldo Cruz, 105 (2010) (7) 843-849.
Kim, et al., "Applications for T-cell epitope queries and tools in the Immune Epitope Database and Analysis Resource" J. Immunol. Methods, 374 (2011) 62-69.
Lasmar, et al., "Evaluating the effectiveness of an inactivated vaccine from Anaplasma marginale derived from tick cell culture", Rev. Bras. Parasitol. Vet., Jaboticabal, 21 (2012) (2) 112-117.
Lopez, et al , "Immunogenicity of Anaplasma marginale Type IV Secretion System Proteins in a Protective Outer Membrane Vaccine", Infection and Immunity, 75 (2007) (5) 2333-2342.
Machado, et al., "An enzyme-linked immunosorbent assay (ELISA) for the detection of antibodies against Babesia bovis in cattle", Veterinary Parasitology, 71 (1997) 17-26.
McGuire, et al., "Recombinant vaccinia virus expression of Anaplasma marginate surface protein MSP-la: effect of promoters, leader sequences and GPI anchor sequence on antibody response", Vaccine, 12 (1994) (5) 465-471.
Morse, et al., "Breadth of the CD4+ T-cell response to Anaplasma marginate VirB9-1, VirB9-2, and VirB10 and MHC class II DR and DQ restriction elements", Immunogenetics, 64 (2012) (7) 507-523.
Morse, et al., "Association and Evidence for Linked Recognition of Type IV Secretion System Proteins VirB9-1, VirB9-2, and VirB10 in Anaplasma marginate", Infection and Immunity, 80 (2012) (1) 215-227.
Noh, et al., "The immunization-induced antibody response to the Anaplasma marginale major surface protein 2 and its association with protective immunity", Vaccine, 28 (2010) (21) 3741-3747.
Noh, et al., "Composition of the Surface Proteome of Anaplasma marginale and Its Role in Protective Immunity Induced by Outer Membrane Immunization", Infection and immunity, 76 (2008) (5) 2219-2226.
Santos, et al., "Epitope-Based Vaccines with the Anaplasma marginale MSP1a Functional Motif Induce a Balanced Humoral and Cellular Immune Response in Mice", PLoS ONE, 8 (2013) (4) e60311.
Silvestre, et al., "Evaluation of humoral and cellular immune response of BALB/c mice immunized with a recombinant fragment of MSP1a from Anaplasma marginale using carbon nanotubes as a carrier molecule", Vaccine, 32 (2014) (19) 2160-2166.
Vita, et al., "The immune epitope database (IEDB) 3.0", Nucleic Acids Res, 43 (2015) D405-412.
Pipano, et al., "Frozen Anaplasma centrale vaccine against anaplasmosis in cattle", Brazilian Journal of Veterinary Research and Animal Science, 142 (1986) (6) 553-556.
Livak et al. "Analysis of relative gene expression data using real-time quantitative PCR and the 2-$\Delta\Delta$CT method", Methods, 25 (2001) 402-408.
Andrade, et al., "Immunization of cattle using a DNA vaccine (pcDNA3.1/MSP1b) prepared from the Jaboticabal strain of Anaplasma marginale", Annals of New York Academy of Sciences, New York, 1026 (2004) 257-266.
Carelli, et al., "Detection and quantification of Anaplasma marginale DNA in blood samples of cattle by real-time PCR", Veterinary Microbiology, 124 (2007) 7-14.
Hartree, et al., "Determination of protein: a modification of the Lowry method that gives a linear photometric response", Analytical Biochemistry, 48 (1972) 422-427.
Puech, et al., "Design and evaluation of a unique SYBR Green real-time RT-PCR assay for quantification of five major cytokines in cattle, sheep and goats", BMC Veterinary Research, 11 (2015) (65).
De Lollo, et al., "Impaired CD8(+) T cell responses upon Toll-like receptor activation in common variable immunodeficiency", Journal of Translational Medicine, 14 (2016) (1) 138.
Konnai, et al., "The rapid quantitative analysis of bovine cytokine genes by real-time RT-PCR", Veterinary Microbiology, 94 (2003) 283-294.
Barbosa Da Silva, et al., "Molecular and serological prevalence of Anaplasma marginale in water buffaloes in northern Brazil", Ticks and Tick-Borne Diseases, 5 (2014) 100-104.
Byrne, et al., "A standardized gating technique for the generation of flow cytometry data for normal canine and normal feline blood lymphocytes", Veterinary Immunology and Immunopathology, 73 (2000) 167-182.
Palmer, et al., "Antigenic variation in the persistence and transmission of ehrlichia Anaplasma marginale", Microbes and Infection, 2 (1999) 167-176.
Eriks et al., "Detection and quantification of Anaplasma marginale in carrier cattle by using a nucleic acid probe", Journal of Clinical Microbiology, 27 (1989) 279-284.
French, et al., "Expression of Anaplasma marginale major surface protein 2 variants during persistent cyclic rickettsemia", Infection and Immunity, 66 (1998) 1200-1207.

(56) References Cited

OTHER PUBLICATIONS

Brayton, et al., "Simultaneous variation of the immunodominant outer membrane proteins, msp2 and msp3, during Anaplasma marginale persistence in vivo", Infection and Immunity, 71 (2003) 6627-6632.

Futse, et al., "Generation of Antigenic Variants via Gene Conversion: Evidence for recombination fitness selection at the locus level in Anaplasma marginale", Infection and Immunity, 77 (2009) 3181-3187.

HYBRID PEPTIDE, SET OF HYBRID PEPTIDES, COMPOSITION, USES OF THE HYBRID PEPTIDE, METHOD FOR INDUCING AN IMMUNE RESPONSE AND KITS

RELATED APPLICATIONS

The present application is the U.S. National Stage of International Patent Application No. PCT/BR2018/050024, filed Feb. 9, 2018, which is hereby incorporated by reference in its entirety, and which claims priority to Brazilian Patent Application No. BR 10 2017 002668-0, filed Feb. 9, 2017.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to new hybrid peptides, developed from the combination of peptide fragments of membrane surface proteins present on causative microorganisms of anaplasmosis in particular bacteria of the species *Anaplasma marginale*. The present invention further relates to sets of hybrid peptides, the compositions and the kits comprising these novel hybrid peptides, the uses thereof and the method for inducing immune response.

Each hybrid peptide according to the present invention comprises two or more peptide fragments of amino acid sequences as defined in the present invention linked together by means of a spacer element. The peptide fragments combined are peptide fragments of the proteins MSP1, MSP1a, MSP1b, MSP2, MSP2-HRV, MSP3, OMP7, OMP8, and VirB9 and virB10.

BACKGROUND OF THE INVENTION

Anaplasmosis is a hemolytic disease caused mainly by bacteria of the genus *Anaplasma*, and in particular, *Anaplasma marginale*, which can be transmitted in various ways. More commonly, transmission can occur mechanically through arthropods (such as blood-eating flies) and through contaminated instruments (such as needles, bovine tattooing instruments, dehorning equipment, among others); biologically (by tick vectors); via iatrogenic route; or transplacentally. Several ruminants such as cattle, buffalos, bison, antelope, deer, among others, as well as, to a lesser extent, humans can become infected by these bacteria. In humans, *A. phagocytophilum* is reported to cause human granulocytic anaplasmosis. The contribution of each transmission factor will depend on the animal concerned and the geographical region in which they are found.

In particular, the infection of cattle herds by bacteria of the species *Anaplasma marginale* (Rickettsiales: Anaplasmataceae) has a significant economic impact on the livestock sector. This is due to high morbidity and mortality rates, leading to the loss of millions of dollars a year. In cattle, erythrocytes correspond to the only site of infection. Upon detection of erythrocytic infection, the number of parasitized erythrocytes increases exponentially, leading to anemia and jaundice. In addition, clinical symptoms include fever, lethargy, weight loss, reduced milk production and miscarriage, often leading to animals older than 2 years to death.

Following the initial infection, the incubation period is 17-45 days. *A. marginale* invades erythrocytes and initiates replication cycles. Infected erythrocytes are removed by the reticuloendothelial system and subsequent reinvasion of erythrocytes. During the initial infection there is a geometric increase in which the number of infected red blood cells doubles every 24 hours. During the acute phase, the number of infected erythrocytes can be as high as $10^9$ cells per mL of blood (Palmer et al., 1999).

Depending on the *A. marginale* strain and host susceptibility, from 10% to 90% of erythrocytes may be parasitized in the acute phase of infection. The concentration of infected erythrocytes varies markedly at two-month intervals from $10^3$ to $10^5$ infected cells per mL of blood (Eriks et al., 1989), much lower than in the acutely infected animal ($>10^9$). Since the average red cell life is 160 days, to maintain persistent infection, new red blood cells must be reinfected continuously. This is accompanied by the mechanism of immune response evasion in a persistently infected reservoir, followed by emergence and replication of *A. marginale* antigenic variants. Each cycle reflects the emergence of one or more, commonly multiple clones expressing the single hypervariable region (HVR) of MSP2 (French et al., 1998) and MSP3 (Brayton et al., 2003; Futse et al., 2009). These "escape variants" are not recognized by antibodies present in the emergence period and are concomitantly controlled by the development of IgG2 directed to the specific HVR region of MSP2 and MSP3 (Palmer et al., 2000). This emergency and control cycle continues unabated allowing persistent infection throughout life (Palmer et al., 2006).

The costs of treatments are significant, and the treatments themselves are not always effective. The measures of management of illness consist mainly in combating biological vectors and blood-eating flies, for example, with the use of acaricides and fly-killers respectively. But also in the administration of antibiotics, in blood transfusions in highly infected animals, in the administration of drugs to encourage the production of new erythrocytes, and in vaccination. As it is considered the most effective and economical measure among those mentioned, vaccination is usually the chosen form for the control of bovine anaplasmosis. However, currently available vaccines are scarce and have many disadvantages.

Traditional approaches to vaccine development for anaplasmosis control are basically of two types: from living or attenuated organisms and from dead or inactivated organisms. Both only partially protect and induce protective immunity that reduces or prevents clinical disease but not prevent cattle from becoming persistently infected with *A. marginale*—serving as reservoirs.

Other disadvantages of traditional anaplasmosis vaccine design approaches are as follows: they are laborious, time-consuming, non-standardized, costly and essentially rudimentary processes of production. In addition, they are essentially dependent on biological material, which is why they incur all the disadvantages just mentioned, not allowing the production of large-scale vaccines. In addition, when they are based on blood, they confer inherent risk of contamination by other pathogens. In general, they can induce antibody production without conferring immunoprotection.

For example: US Patent Document U.S. Pat. No. 3,511,908 A discloses an anaplasmosis vaccine production method, which includes the steps of exsanguination of infected bovine, mixing of anticoagulant with the obtained blood, centrifugation of anticoagulated blood to sediment the erythrocytes without rupture thereof, erythrocyte suspension in physiological saline solution, ultrasonication of the suspended solution for erythrocyte rupture and release of the anaplasma bodies without destruction thereof, centrifugation of the suspended solution to sediment the anaplasma bodies, suspension of the anaplasma bodies in distilled water and finally, lyophilization of the anaplasma bodies to obtain antigens. The antigens thus obtained are mixed in adjuvant and used for immunization of the animals.

The US Patent Document U.S. Pat. No. 3,674,860 discloses method of producing anaplasmosis vaccine from attenuated strains of *A. marginale* bacteria, which includes the steps of exposure of infected bovine erythrocytes to radiation, inoculation of such irradiated cells into susceptible non-bovine ruminant host (deer, sheep or goats), culture of blood of such host containing attenuated *A. marginale* bacteria, serial inoculation of the blood grown in a plurality of said hosts, continuation of said inoculation in series so that the bacteria *A. marginale* are confirmed as attenuated in cultured blood through specific tests and cultivating said hosts blood with bacteria confirmed as attenuated. Blood containing attenuated *A. marginale* bacteria is then used for vaccination of animals.

The U.S. Pat. No. 4,956,278 discloses method of vaccine production against anaplasmosis, so that it does not induce neonatal hemolysis, and includes the steps of selectively lysing erythrocytes infected with *A. marginale*, concentration of *A. marginale* and lysed erythrocytes while there is separation of the leukocytes present therein, subjecting the concentrate to fractionation under pressure to release the initial *A. marginale* bodies, concentration of such bodies by gradient centrifugation, cultivation and washing thereof for obtaining them in a substantially pure form. Such purified bodies are used for vaccination of animals.

Lasmar et al. (2012) tested inactivated *A. marginale* vaccine grown on tick cell culture *Ixodes scapularis* IDE8. Tick cells were infected with blood containing bacterial isolates. About 14 days after inoculation, *A. marginale* colonies were observed and subsequent infection of cells was obtained by transferring infected cells to uninfected cells. When the infection level reached 70 to 80% of the cells, they were centrifuged, the cell button formed was homogenized and incubated with trypsin, the *A. marginale* initial bodies of the supernatant were quantified, dose adjusted and inactivated. Subsequently, the antigens were emulsified in adjuvant, stirred and incubated at room temperature for further vaccination of the animals.

Hammac et al. (2013) obtained an experimental vaccine from suspension of intact, fresh and not purified *Ixodes scapularis* ISE6 tick cells infected with strains of *A. marginale*.

In other approaches to vaccination, the strategy was directed to the role of membrane surface proteins of microorganisms responsible for the infection. The membrane surface proteins of such microorganisms, such as major surface proteins—MSP—or outer membrane proteins—OMPs—play a crucial role in the process of erythrocyte infection and survival of rickettsia in the host. Therefore, such approaches have also been the object of research and development of experimental anaplasmosis vaccines.

Although some of the experimental studies and developments in this direction, with more or less satisfactory results, have partly improved the disadvantages of traditional vaccination methods, they have not been ideal, either from an immunization standpoint or from a process of large scale manufacturing standpoint.

According to Palmer et al (1989), cattle immunized with the native surface proteins of *A. marginale* MSP1 and MSP2 were partially protected against homologous or heterologous challenge with strain of virulent *A. marginale* (Palmer et al., 1989).

In 1995, Palmer and McElwain demonstrated that native surface protein MSP1a did not confer protection to vaccinated animals (Palmer; McElwain 1995).

The US Patent Document U.S. Pat. No. 6,979,451, for example, discloses method of producing anaplasmosis vaccine from a composition comprising the recombinant MSP1a main surface protein combined or not with an antigenic preparation derived from IDE8 tick cell line infected with *A. marginale*.

In 2005, Abbot et al found that the MSP2 surface native protein associated to interleukin 12 (IL-12) and adjuvants, that stimulate the immune response of the Th1 type (cellular; production of cytokines) in cattle, did not stimulate protective response against homologous challenge with *A. marginale* (Abbott et al., 2005).

Lopez et al. (2005) did not verify immunoprotection against external membrane proteins OMP. However, sera from cattle immunized with *A. marginale* membrane recognized the outer membrane proteins OMP4, OMP7, OMP10 and OMP14.

Brayton et al. (2005) demonstrated that the proteins OMP4, OMP7, OMP10 and OMP14 were recognized by sera from cattle immunized with *A. marginale* membrane and, therefore, would be promising for immunogen development.

The association of MSP1a recombinant proteins (C-terminal region) and MSP2 in adjuvant (CpG ODN 2006) did not provide protection against heterologous challenge, despite significant production of total immunoglobulin G (IgG) against both proteins, and IgG2 against MSP1a (Araújo, 2005).

Kawasaki et al. (2007) demonstrated that a vaccine containing recombinant protein subunits MSP1a, MSP1b, MSP4 and MSP5, in ISCOM and Freund adjuvant induced humoral response in BALB/c mice, suggesting that a vaccine containing recombinant MSP proteins could be efficient in acute infection.

Agnes et al. (2011) and Noh et al. (2008) tested the membrane fractions of *A. marginale* containing different proteins of surface membrane, MTO and MSP. As a result, they verified IgG2 antibody production and reduced bacteremia.

Immunogenicity tests of recombinant MSP1a fragments in BALB/c mice indicated humoral and cellular response stimulation, IgG2 antibody production and pro-inflammatory cytokine release (Santos et al., 2013; Silvestre et al., 2014).

Finally, attention should be drawn to virulence factors, which are secreted by a complex present in such microorganisms called T4S S (type IV secretion system proteins), which promotes host cell invasion and intracellular survival of microorganisms. Trials conducted in cattle demonstrated that VirB9 and VirB10 factors of bacteria stimulate both cellular and humoral immune response (Lopez et al., 2007, Araújo et al, 2008; Morse et al, 2012a; Morse et al, 2012b).

Lopez et al. (2007) immunized cattle with fractions of the *A. marginale* outer membrane and found antibody production against virulence factors secreted by the Rickettsia T4SS complex, increased T lymphocyte proliferation and interferon-gamma secretion (INF-gamma).

The spite of the increase in the scientific knowledge about the role of these proteins in infectivity of cells by microorganisms, as well as the ability to induce an immune response (which may or may not be associated with the protection and/or reducing symptoms of immunized animals) approaches hitherto not proved promising enough for the manufacture of one vaccine against anaplasmosis, in large scale, so that improved strategies are more efficient and/or productive of immunization, especially for large scale vaccination, are still needed.

In this regard, to meet the needs of the prior art, the present invention has been developed, which discloses novel peptide entities or constructs (hybrid peptides) as vaccine epitopes, in particular against anaplasmosis. Hybrid peptides according to the present invention used, for example, for vaccination of cattle against anaplasmosis, have allowed the protection of animals. In addition to the very high efficiency, the use of synthetic peptides allows complete independence of biological material use for their manufacture, enabling the desired large scale production and, therefore, at least partially solving the aforementioned disadvantages of the state of the art. Combining efficacy with a large-scale production vaccine against anaplasmosis represents, a thus far not obtained, major advance over the state of the art.

BRIEF DESCRIPTION OF SEQUENCES

SEQ ID NO: 1 refers to the sequence of a peptide fragment of the MSP1a protein.

SEQ ID NO: 2 refers to the sequence of a peptide fragment of the MSP1b protein.

SEQ ID NO: 3, SEQ ID NO: 4 and SEQ ID NO: 5 refer to the peptide fragment sequences of the MSP1 protein.

SEQ ID NO: 6, SEQ ID NO: 7, SEQ ID NO: 8, SEQ ID NO: 9 and SEQ ID NO: 10 refer to the peptide fragment sequences of the MSP2 protein.

SEQ ID NO: 11 and SEQ ID NO: 12 refer to the peptide fragment sequences of the MSP2-HRV protein.

SEQ ID NO: 13 refers to the sequence of a peptide fragment of the MSP3 protein.

SEQ ID NO: 14 refers to the sequence of a peptide fragment of the OMP8 protein.

SEQ ID NO: 15 refers to the sequence of a peptide fragment of the OMP7 protein.

SEQ ID NO: 16 and SEQ ID NO: 17 refer to the VirB9 protein peptide fragment sequences.

SEQ ID NO: 18 and SEQ ID NO: 19 refer to the VirB10 protein peptide fragment sequences.

SEQ ID NO: 20 refers to the hybrid peptide derived from binding of the peptide fragments of the sequences SEQ ID NO: 5 and SEQ ID NO: 6, by means of a spacer element consisting of 4 residue glycine according to the (SEQ ID NO: 5)-GGGG-(SEQ ID NO: 6) construct (P28).

SEQ ID NO: 21 refers to the hybrid peptide derived from binding of the peptide fragments of the sequences SEQ ID NO: 3 and SEQ ID NO: 17 by means of a spacer element consisting of 3 glycine residues according to the construct (SEQ ID NO: 3)-GGG-(SEQ ID NO: 17) (P41).

SEQ ID NO: 22 refers to the hybrid peptide derived from the binding of the peptide fragments of the sequences SEQ ID NO: 13 and SEQ ID NO: 12 by means of a spacer element consisting of 3 glycine residues according to the construct (SEQ ID NO: 13)-GGG-(SEQ ID NO: 12) (P42).

SEQ ID NO: 23 refers to the hybrid peptide derived from the binding of the peptide fragments of the sequences SEQ ID NO: 14 and SEQ ID NO: 15 by means of a spacer element consisting of 4 glycine residues according to the construct (SEQ ID NO: 14)-GGGG-(SEQ ID NO: 15) (P44).

SEQ ID NO: 24 refers to the hybrid peptide derived from the binding of the peptide fragments of the sequences SEQ ID NO: 14 and SEQ ID NO: 16 by means of a spacer element consisting of 4 glycine residues according to the construct (SEQ ID NO: 14)-GGGG-(SEQ ID NO: 16) (P50).

SEQ ID NO: 25 refers to the hybrid peptide derived from the binding of the peptide fragments of the sequences SEQ ID NO: 13 and SEQ ID NO: 19 by means of a spacer element consisting of 4 glycine residues according to the construct (SEQ ID NO: 13)-GGGG-(SEQ ID NO: 19) (P51).

SEQ ID NO: 26 refers to the hybrid peptide derived from the binding of the peptide fragments of the sequences SEQ ID NO: 5, SEQ ID NO: 6 and SEQ ID NO: 17, by means of a spacer element between fragments consisting of 4 glycine residues, according to construct (SEQ ID NO: 5)-GGGG-(SEQ ID NO: 6)-GGGG-(SEQ ID NO: 17) (P53).

SEQ ID NO: 27 refers to the hybrid peptide derived from the binding of the peptide fragments of the sequences SEQ ID NO: 1 and SEQ ID NO: 18 by means of a spacer element consisting of 4 glycine residues according to the construct (SEQ ID NO: 1)-GGGG-(SEQ ID NO: 18) (P54).

SEQ ID NO: 28 refers to the hybrid peptide derived from the binding of the peptide fragments of the sequences SEQ ID NO: 4 and SEQ ID NO: 18 by means of a spacer element consisting of 4 glycine residues according to the construct (SEQ ID NO: 4)-GGGG-(SEQ ID NO: 18) (P48).

SEQ ID NO: 29 refers to the hybrid peptide derived from the binding of the peptide fragments of the sequences SEQ ID NO: 2, SEQ ID NO: 14 and SEQ ID NO: 17, by means of a spacer element between fragments consisting of 4 glycine residues according to the construct (SEQ ID NO: 2)-GGGG-(SEQ ID NO: 14)-GGGG-(SEQ ID NO: 17) (P73).

SEQ ID NO: 30 refers to the hybrid peptide derived from the binding of the peptide fragments of the sequences SEQ ID NO: 7 and SEQ ID NO: 18 by means of a spacer element consisting of 4 glycine residues according to the construct (SEQ ID NO: 7)-GGGG-(SEQ ID NO: 18) (P55).

SEQ ID NO: 31 refers to the hybrid peptide derived from the binding of the peptide fragments of the sequences SEQ ID NO: 8 and SEQ ID NO: 16 by means of a spacer element consisting of 5 glycine residues, according to the construct (SEQ ID NO: 8)-GGGGG-(SEQ ID NO: 16) (P 52).

SEQ ID NO: 32 refers to the hybrid peptide derived from the binding of the peptide fragments of the sequences SEQ ID NO: 9 and SEQ ID NO: 18 by means of a spacer element consisting of 4 glycine residues according to the construct (SEQ ID NO: 9)-GGGG-(SEQ ID NO: 18) (P57).

SEQ ID NO: 33 refers to the hybrid peptide derived from the binding of the peptide fragments of the sequences SEQ ID NO: 11, SEQ ID NO: 1 and SEQ ID NO: 15, by means of a fragment spacer between the fragments consisting of 4 glycine residues according to the construct (SEQ ID NO: 11)-GGGG-(SEQ ID NO: 1)-GGGG-(SEQ ID NO: 15) (P68).

SEQ ID NO: 34 refers to the 5'-3' forward oligonucleotide (forward or F) of the interleukin-2 (IL-2) encoding gene (Table 5) used in the Quantitative Real Time PCR experiment.

SEQ ID NO: 35 refers to the IL-2 5'-3' (reverse or R) reverse oligonucleotide (Table 5) used in the Quantitative Real Time PCR experiment.

SEQ ID NO: 36 refers to the 5'-3' direct oligonucleotide of the interferon-γ (IFN-γ) encoding gene (Table 5) used in the Quantitative Real Time PCR experiment.

SEQ ID NO: 37 refers to the 5'-3' inverse oligonucleotide of IFN-γ (Table 5) used in the Quantitative Real Time PCR experiment.

SEQ ID NO: 38 refers to the 5'-3' direct oligonucleotide of the gene encoding tumor necrosis factor-α (TNF-α) (Table 5) used in the Quantitative Real Time PCR experiment.

SEQ ID NO: 39 refers to the 5'-3' inverse oligonucleotide of TNF-α (Table 5) used in the Quantitative Real Time PCR experiment.

SEQ ID NO: 40 refers to the 5'-3' direct oligonucleotide of the interleukin-12 (IL-12) encoding gene (Table 5) used in the Quantitative Real Time PCR experiment.

SEQ ID NO: 41 refers to the 5'-3' inverse oligonucleotide of IL-12 (Table 5) used in the Quantitative Real Time PCR experiment.

SEQ ID NO: 42 refers to the 5'-3' direct oligonucleotide of the interleukin-10 (IL-10) encoding gene (Table 5) used in the Quantitative Real Time PCR experiment.

SEQ ID NO: 43 refers to the 5'-3' inverse oligonucleotide of IL-10 (Table 5) used in the Quantitative Real Time PCR experiment.

SEQ ID NO: 44 refers to the 5'-3' direct oligonucleotide of the gene encoding H3histone, family 3A (H3F3A) (Table 5) used in the Quantitative Real Time PCR experiment.

SEQ ID NO: 45 refers to the 5'-3' inverse oligonucleotide of H3F3A (Table 5) used in the Quantitative Real Time PCR experiment.

SEQ ID NO: 46 refers to 5'-3' direct oligonucleotide of the gene encoding MSP1b of *Anaplasma marginale* used in the Quantitative Real Time PCR experiment.

SEQ ID NO: 47 refers to the 5'-3' reverse oligonucleotide of *Anaplasma marginale* MSP1b used in the Quantitative Real Time PCR experiment.

SEQ ID NO: 48 refers to the 5'-3' oligonucleotide of the hydrolysis probe used in the Quantitative Real Time PCR Experiment.

BRIEF DESCRIPTION OF THE INVENTION

The present invention relates to novel hybrid peptides developed from the combination of membrane surface protein peptide fragments present in anaplasmosis-causing microorganisms, in particular bacteria of the *Anaplasma marginale* species. The fragments were defined as vaccine epitopes from the inventors' rational approach with the aid of immunogenicity database. The present invention further relates to hybrid peptide assemblies, to compositions and to kits comprising such novel hybrid peptides, their uses and methods of inducing immune response.

Thus, a first object of the present invention is a hybrid peptide comprising two or more peptide fragments having the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

A preferred embodiment of the present invention is a hybrid peptide comprising two or three peptide fragments having the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

Preferably, said spacer element consists of one or more glycine residues or one or more proline residues or any combinations thereof. More preferably, the spacer element is comprised of 2 to 15 glycine residues, particularly 2 to 10 glycine residues, more particularly 3 to 5 glycine residues.

Another preferential embodiment of the present invention is the hybrid peptide consisting, each, of the amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33, preferentially in the amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27.

A second object of the present invention is a hybrid peptide set comprising at least two hybrid peptides as defined by the present invention. For example, it is a hybrid peptides set, comprising at least two hybrid peptides, wherein each hybrid peptide comprises two or more peptide fragments of amino acid sequences of SEQ ID NO: 1, SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

Preferably, each hybrid peptide of the hybrid peptide set comprises two or three peptide fragments having the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

The spacer element of each hybrid peptide of the hybrid peptide set is one or more glycine residues or one or more proline residues or any combinations thereof. More preferably, the spacer element is comprised of 2 to 15 glycine residues, particularly 2 to 10 glycine residues, more particularly 3 to 5 glycine residues.

In a preferred embodiment of the present invention, the hybrid peptides set comprises at least two hybrid peptides of the amino acid sequences of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33, more preferably from the amino acid sequences SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27.

In another preferred embodiment of the present invention, the hybrid peptide set comprises all hybrid peptides of the amino acid sequences of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27.

In yet another preferred embodiment of the present invention, the hybrid peptide set comprises at least two hybrid peptides of the amino acid sequence of SEQ ID NO: 20, SEQ ID NO: 21, SEQ ID NO: 23, SEQ ID NO: 25 and SEQ ID NO: 26. Preferably, the hybrid peptides set comprises all hybrid peptides of amino acid sequences of SEQ ID NO: 20, SEQ ID NO: 21, SEQ ID NO: 23, SEQ ID NO: 25 and SEQ ID NO: 26

A third object of the present invention is a composition comprising at least one hybrid peptide as defined by the present invention. For example, it is a composition comprising at least one hybrid peptide, wherein the at least one hybrid peptide comprises two or more peptide fragments having the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

Preferably, the at least one hybrid peptide of the composition comprises two or three peptide fragments having the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19, linked together by means of a spacer element.

The spacer element of the at least one hybrid peptide of the composition consists of one or more glycine residues or one or more proline residues or any combinations thereof. More preferably, the spacer element is comprised of 2 to 15 glycine residues, particularly 2 to 10 glycine residues, more particularly 3 to 5 glycine residues.

In a preferred embodiment of the present invention, the composition comprises at least one hybrid peptide, wherein the at least one hybrid peptide, each, consists of the amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 and SEQ ID NO: 33.

In another preferred embodiment of the present invention, the composition comprises at least one hybrid peptide, wherein the at least one hybrid peptide, each, consists of the amino acid sequence of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27. Preferably, the composition of the present invention comprises from 2 to 8 hybrid peptides, preferably from 3 to 7 hybrid peptides, more preferably 4 to 6 hybrid peptides.

The composition according to the present invention preferably comprises one or more diluents and/or one or more pharmaceutically acceptable excipients and/or one or more additional biologically active compounds.

The composition according to the present invention preferably comprises one or more additional adjuvants. Preferably, the one or more adjuvants are selected from Freund's complete adjuvant, Freund's incomplete adjuvant, aluminum hydroxide, silica and saponin. Even more preferably, one or more adjuvants are selected from Freund's complete adjuvant and Freund's incomplete adjuvant.

The composition according to the present invention, is preferably in the form of solution, mixture, powder, granules, aerosol, or lyophilized.

In a preferred embodiment of the present invention, the composition is a vaccine, particularly to immunize, treat, protect, alleviate and/or prevent disease or symptoms of disease and/or new infections with absence or reduction of clinical symptoms caused by bacteria, rickettsias, or protozoa, wherein the bacteria are particularly of the genus *Anaplasma*, more particularly *Anaplasma marginale*, and wherein the protozoa are particularly *Babesia bovis* or *Babesia bigemina*.

Preferably, bacteria, rickettsia or protozoa are transmitted by arthropods, by mechanical infection via iatrogenic or via transplacental, wherein the arthropods are particularly ticks or insects, more particularly ticks. Preferably, the tick is of the family Ixodidae, particularly of the genus *Rhipicephalus* spp., more particularly the *Rhipicephalus* (*Boophilus*) micro plus.

A fourth object of the present invention is the use of at least one hybrid peptide as defined by the present invention for the manufacture of a composition as defined by the present invention. Preferably, the composition of the present invention is to immunize, to treat, to protect, to mitigate and/or to prevent diseases or symptoms of diseases and/or new infection with the absence or reduction of clinical symptoms, caused by bacteria, particularly of the genus *Anaplasma*, more particularly *Anaplasma marginale*, in a human or animal, particularly a ruminant, more particularly a bovine.

A fifth object of the present invention is the use of at least one hybrid peptide as defined by the present invention in an in vitro cell culture process.

A sixth object of the present invention is the use of at least one hybrid peptide as defined by the present invention for diagnosis.

A seventh object of the present invention is a method of inducing an immune response comprising administering a therapeutically effective amount of the composition, as defined by the present invention to a human or animal. Preferably, the therapeutically effective amount is from 50 to 150 µg, more preferably from 80 to 130 µg, most preferably 100 µg, of each hybrid peptide per human or animal. Preferably, the immune response is to immunize, to treat, to protect, to mitigate and/or to prevent diseases or symptoms of diseases and/or new infections with the absence or reduction of clinical symptoms, caused by bacteria, particularly of the genus *Anaplasma*, more particularly *Anaplasma marginale*, in an animal, particularly in a ruminant, more particularly in a bovine. Preferably, the immune response is by the aid of a carrier.

An eighth object of the present invention is a kit comprising at least one hybrid peptide as defined by the present invention. A ninth object of the present invention is a kit comprising a composition as defined by the present invention. Preferably, the kits are the eighth and ninth objects are for diagnosis and/or vaccination.

Any one of the objects or their preferred embodiments described above can serve as a basis to make other objects and their preferred embodiments, even if this (these) relation(s) has (have) not been explicitly described.

The inventors of the present invention have found that by vaccinating cattle with the hybrid peptides as defined herein, animal protection has been achieved.

DETAILED DESCRIPTION OF THE INVENTION

Definitions

Unless otherwise defined, all terms of the art, notations, and other scientific terminology used herein are intended to have the meanings commonly understood by those skilled in the art in the field of the present invention. In some cases, terms with commonly understood meanings are defined herein for the purpose of clarity and/or prompt reference, and the inclusion of such definitions herein should not necessarily be construed as representing a substantial difference in relation to what is generally understood in the state of the art.

The techniques and procedures described or referred to herein are generally well understood and employed using conventional methodology by those skilled in the art. As appropriate, the processes involving the use of commercially available kits and reagents are generally performed according to protocols and/or parameters defined by the manufacturer, unless otherwise indicated.

It is noteworthy that the present invention, where appropriate, is not limited to the described methodology, protocols, cell line, genus or species of animals, constructs and reagents, which obviously may vary. Furthermore, the terminology used herein is for the purpose of describing examples of specific embodiments only, and is not intended to limit the scope of the present invention.

Throughout the present document, the singular forms "a", "an" and "the," or singular form of any term or phrase, include references to the plural, unless the context clearly dictates otherwise.

Throughout the present document, the word "comprise", and any variations such as "comprises" or "comprising", must be interpreted as "open terms", wherein it may imply in the inclusion of elements or groups of additional elements, which have not been explicitly described, having no limitative character.

Throughout the present document, the word "consist" and any variations such as "consists" or "consisting" shall be construed as "closed terms" and may not imply the inclusion of additional elements or groups of elements which were not explicitly described, having a limiting character.

Throughout the present document, the exact values or exact value ranges provided with respect to a particular factor, quantity, concentration, or preference shall be construed as also providing corresponding approximate values or ranges, such as by the expression "about"

Throughout the present document, words and phrases such as "preferably", "particularly", "for example", "as", "such as", "more particularly" and the like, and their variations, shall be construed as entirely optional features, preferred embodiments or possible non-exhaustive examples without limiting scope.

Throughout the present document, all headings and subheadings are used for convenience only and should not be construed as limiting the present invention.

Throughout the present document, the word "peptide" is to be interpreted as a single linear chain of amino acid monomers linked by peptide links. Amino acids that have been incorporated into peptides are called "residues". Each peptide has an N-terminal residue and a C-terminal residue at the corresponding ends of the peptide. Also, throughout the present document, the word "peptide" should be interpreted as comprising any number of consecutive residues. Furthermore, the words "peptide", "polypeptide" and "protein" should be understood as synonymous, they may be interchangeable with each other and should not be interpreted as having a certain number of residues.

Throughout the present document, the term "hybrid peptide" should be understood as a peptide originated by joining, bonding, union or connection of two or more same or different peptide fragments, as defined by the present invention, in any order, in that such joining, bonding, union or connection between peptide fragments is accomplished by means of a spacer element. Peptide-spacer element bonding is preferably performed by peptide bonding.

Furthermore, throughout the present document, the words "peptide", "hybrid peptide", "polypeptide", "peptide fragment" and "protein" shall be construed as having any shape, being linear or having three-dimensional native conformation or particular of interest. The peptide fragments to be bonded may be derived from microorganisms of the same species or different species. In addition, peptide fragments and hybrid peptides may be synthetically synthesized (e.g. by solid phase synthesis techniques), recombinant-originated (e.g. by using expression cassette under the control of a specific promoter) or from any pertinent technologies of the field of the invention known by a person skilled in the art. Sufficient techniques to guide it are also found in the literature.

According to the present invention, structural modifications to improve the in vivo stability of the peptides, as well as to improve the molecular properties related to the mechanism of action, resulting in improved pharmacological activity (peptideomimetics), if any, should be considered as within the scope of the present invention.

Such modifications may be specifically limited to protecting or replacing the labile bond (peptide bond) by introducing atypical (non-peptide) fragments/portions, or even altering the conformation of the peptide. Promising (non-peptide) molecular modifications would be those that attempt to mimic the molecular structure and properties of the peptide.

Examples of possible molecular modifications would be (Gentilucci et al., 2010): pseudopepdides, which show modification in the backbone of at least one peptide bond with isosteric or isoelectronic groups, such as reduced amides, azopeptides, retro-inverse peptides, peptoides; substitution by unnatural amino acids, such as substitution of L-amino acids by their D-enantiomers; use of N-alkyl amino acids, alpha-substituted alpha amino acids, beta-substituted alpha amino acids, proline, gamma- and beta amino acids analogs; cyclization, such as macrolactones; ether, biaryl, disulfide or other bridges that mimic those already mentioned; linking the N and C terminal portion of the main chain, or the N or C terminal portion with amino acid side chains.

Moreover, a person skilled in the art will recognize that conservative substitutions that result in the alteration of one amino acid by another chemically similar amino acid in a sequence are within the scope of the present invention. Such conservative substitutions providing functionally similar amino acids are known in the art.

Throughout the present document, the term "spacer element" is to be interpreted as a peptide joining, binding, union or connection element as defined by the present invention. For example, the spacer element can be constituted by one or more glycine residues (Gly or G) or one or more residues proline (Pro or P), or any combinations thereof. For example, the spacer element could be GPGPG. Preferably, the spacer element consists of one or more glycine residues. More particularly, the spacer element consists of 2 to 15 glycine residues, particularly 2 to 10 glycine residues, more particularly 3 to 5 glycine residues. Such glycine residues were selected to confer conformational freedom (flexibility) to the resulting hybrid peptide without impacting the predicted action. Thus, the nature of the spacer element is not of particular relevance or critical to the present invention. In this regard, it should be understood in accordance with the present invention that any spacer element that confers to the resulting hybrid peptide equivalent function, is within the scope of the present invention.

Throughout the present document, the term "hybrid peptide set" shall be construed as a cluster, sampling or aggregate comprising at least two hybrid peptides as defined by the present invention. In this context, the term "at least two" refers to the amount of 2 to 30 hybrid peptides, as well as any range between such values. Preferably, the hybrid peptide set according to the present invention comprises from 2 to 8 hybrid peptides, particularly from 3 to 7 hybrid peptides, more particularly from 4 to 6 hybrid peptides.

Throughout the present document, the word "diluent" should be interpreted as any substance that has the function of diluting, preserving the properties of what is being diluted. Thus, it should be understood in accordance with the present invention that any conventional diluent in any form, usually employed for diluting, is within the scope of the present invention. Acceptable diluents are known by a person skilled in the art. The diluent includes, but is not limited to: water, alcohol and sterile solutions.

Throughout the present document, the term "pharmaceutically acceptable excipient" shall be construed as any carrier, or substance other than a pharmaceutically active ingredient. Thus, it should be understood, in accordance with the present invention, that any conventional pharmaceutically acceptable excipient, in any form, usually employed to act as an excipient, is within the scope of the present invention. Pharmaceutically acceptable excipients are duly known by a person skilled in the art and may be chosen from *Remington: The Science and Practice of Pharmacy*, Remington, 22th edition or *Handbook of Pharmaceutical Excipients*, Rowe, 8th edition, incorporated in the present document as reference. The pharmaceutically acceptable excipient includes, but is not limited to: buffer or saline, stabilizer, surfactant, solubilizer, emulsifier and preservative.

Throughout the present document, the word "adjuvant" mast be interpreted as any substance that modulates or enhances the immunogenicity of the hybrid peptides of the present invention. Thus, it should be understood in accordance with the present invention that any conventional adjuvant in any form, usually employed in compositions for this purpose is within the scope of the present invention. The adjuvant includes, but is not limited to: complete Freund's adjuvant, incomplete Freund's adjuvant, aluminum hydroxide, silica and saponin.

Throughout the present document, the word "carrier" should be interpreted as a carrier, one head group or any structure in which the peptide may be incorporated into or which can be associated with, in order to direct and/or facilitate and/or improve the triggering of an immune response by a human or animal. Thus, it should be understood in accordance with the present invention that any conventional carrier in any form usually employed to act as a carrier is within the scope of the present invention. Suitable carriers are well known by a person skilled in the art. The carrier includes, but is not limited to: particles of colloidal gold, antibodies or antibody fragments, polymers, vesicles and nanovesicles.

Throughout the present document, the term "additional biologically active substance or compound" shall be understood to mean any substance or compound having a biologically active effect. Thus, it should be understood, in accordance with the present invention, that any additional conventional biologically active substance or compound, in any form, usually employed to act as such, is within the scope of the present invention. They may perform their function by the same or similar or different mechanisms. They may have a multiplicity of related action mechanisms and/or have independent action mechanisms. Additional biologically active compounds or substances include, but are not limited to: enhancers, agonists, etc.

Throughout the present document, the term "therapeutically effective quantity" refers to the amount of peptide, which is sufficient to result in a therapeutic effect in said human or animal. The therapeutically effective amount can either be readily determined by a person skilled in the art following routine procedures without undue experimentation, considering the route of administration, the specific composition used, the clinical factors, the age and weight of the human or animal, among others, if applicable, as to be the same regardless of the factors mentioned. Preferably, the therapeutically effective amount is from 50 to 150 µg, more preferably from 80 to 130 µg, most preferably 100 µg, of each human or animal hybrid peptide.

At least one hybrid peptide of the present invention may be used for the manufacture of a composition. In this context, the term "at least one" refers to the amount of 1 to 30 hybrid peptides, as well as any range between such values. Preferably, the at least one hybrid peptide, according to the present invention, comprises from 2 to 8 hybrid peptides, particularly from 3 to 7 hybrid peptides, more particularly from 4 to 6 hybrid peptides.

The composition of the present invention may be formulated according to the standard methodology known by a person skilled in the art and of no particular importance to the present invention. Furthermore, the composition of the present invention may be in any form, considering the function of the composition, the route of administration and the desired effect. Feasible forms include, but are not limited to: solution, mixture, powder, granules, aerosol, or lyophilized.

The composition of the present invention can be administered to a human or animal by several default routes of administration, considering the form of the composition and the desired effect. It may be for predominantly local or systemic effect. The composition of the present invention may, for example, be in the form of solution for subcutaneous administration, in aerosol form for intranasal administration or even in the form of a solution for intramuscular administration, for example, in the neck board region. Other routes of administration include, but are not limited to: oral, topical, implantable, intravenous, intra-arterial, intradermal, intra-peritoneal and parenteral.

The composition of the present invention is preferably a vaccine. Preferably, the form of the vaccine composition of the present invention is solution for intramuscular administration.

The composition of the present invention is preferably to immunize, to treat, to protect, to mitigate and/or to prevent diseases or symptoms of diseases and/or new infections with the absence or reduction of clinical symptoms, caused by bacteria, rickettsia and protozoa. Bacteria and/or rickettsia include, but are not limited to, those of the Alphaproteobacteria class, preferably those of the Anaplasmataceae family, such as *Anaplasma marginale, Anaplasma phagocytophilum, Anaplasma ovis, Anaplasma centrale, Anaplasma bovis*. The protozoans include, but are not limited to, those of the Sarcodine class, preferably those of the order Piroplasmid, such as *Babesia bovis* and *Babesia bigemina*. In particular, the composition of the present invention is to immunize, to treat, to protect, to mitigate and/or to prevent diseases or symptoms of diseases and/or new infections with the absence or reduction of clinical symptoms, caused by bacteria of the genus *Anaplasma*, more particularly *Anaplasma marginale*. In particular, the composition of the present invention is to immunize, to treat, to protect, to mitigate and/or to prevent diseases or symptoms of diseases and/or new infections with the absence or reduction of clinical symptoms, caused by protozoa, particularly *Babesia bovis* and *Babesia bigemine*. In particular, the composition of the present invention is to immunize, to treat, to protect, to mitigate and/or to prevent disease or symptoms of disease and/or new infections with absence or reduction of clinical symptoms caused by bacteria, particularly the genus *Anaplasma*, more particularly *Anaplasma. marginale*, in a human or animal, particularly a ruminant, more particularly a bovine.

Transmission of such bacteria, rickettsia or protozoa can be mechanically or biologically performed by arthropods. Usually, mechanical transmission by arthropods is performed by mosquitoes. Usually, biological transmission by arthropods is performed by ticks. Also, transmission can be performed by mechanical infection through contaminated instruments (such as needles, bovine tattoo instruments, dehorning equipment, among others). Also, transmission can be performed via iatrogenic or transplacental route. Preferentially, the composition of the present invention is to immunize, to treat, to protect, to mitigate and/or to prevent diseases or symptoms of diseases and/or new infections with the absence or reduction of clinical symptoms caused by bacteria or rickettsiae, particularly bacteria of the genus *Anaplasma*, more particularly *A. marginale*, transmitted by tick. Preferably, the tick is of the family Ixodidae, particularly of the genus *Rhipicephalus* spp., more particularly the *Rhipicephalus* (*Boophilus*) *microplus*.

Moreover, at least one hybrid peptide of the present invention may be used for the manufacture of a composition as defined by the present invention by any method known by a person skilled in the art without any undue experimentation. In addition, at least one hybrid peptide of the present invention may be used in an in vitro cell culture process. Such a process includes any process that involves at least one in vitro cell culture step, or wherein all steps are performed in vitro. Such processes include, but are not limited to: processes for making vaccines, reagents, or medicaments, wherein human, plant, animal, or microorganism cell or culture cells are used, such as, for example, in a process that uses tick cell cultures. In addition, at least one hybrid peptide of the present invention may be used for diagnostic purposes. For example, the hybrid peptides of the present invention may be used for diagnosing diseases or conditions associated with the immune response, whether in human or animal.

The composition, according to the present invention, may be used in a method for inducing immune response. In other words, the present invention also relates to a method of inducing an immune response comprising administering a therapeutically effective amount of the composition as defined by the present invention to a human or animal. According to the present document, the term "immune response induction" or just "immune response" should be interpreted as the modulation response, particularly of increased or boosted antibody production by B lymphocytes, T helper cells and/or other immune cells, either directly or indirectly through the coordinated triggering of response, in view of the stimulus given to humans or to animals. Preferably, the immune response is to immunize, to treat, to protect, to mitigate and/or to prevent disease or symptoms of disease and/or new infections with absence or reduction of clinical symptoms. Preferably, the diseases or disease symptoms are caused by bacteria, rickettsia or protozoa. More preferably by bacteria, particularly of the genus *Anaplasma*, more particularly *Anaplasma marginale*. Preferably, the immune response is to immunize, to treat, to protect, to mitigate and/or to prevent disease or symptoms of disease and/or new infections with absence or reduction of clinical symptoms in a ruminant, more particularly in a bovine. Preferably, the immune response may be triggered, assisted or directed by using at least one carrier.

The method of inducing immune response may be by single dose administration or repeated dose administration of the vaccine at predetermined time intervals. Preferably, the administration regimen is by 3-dose immunization, 15 days apart.

In a further embodiment, the present invention provides a kit comprising at least one hybrid peptide of the present invention. In another additional embodiment, the present invention provides a kit comprising at least one composition of the present invention comprising at least one hybrid peptide of the present invention.

Preferably, the kit is for diagnosis, particularly for diagnosis of diseases or conditions associated with the immune response, whether in human or animal. Thus, the kit preferably includes a container, comprising at least one peptide or at least one composition according to the present invention, and instructions for use and/or at least a second container with another composition, such as a reagent, particularly a detection reagent, such as an antibody. Preferably, it further includes an instrument or device for diagnostic assistance.

In another embodiment of the present invention, the kit is preferably for vaccination. Preferably, the vaccine is to immunize, to treat, to protect, to mitigate and/or to prevent disease or symptoms of disease and/or new infections with absence or reduction of clinical symptoms caused by bacteria, rickettsia or protozoa, wherein the bacteria are particularly of the genus *Anaplasma*, more particularly *Anaplasma marginale*, and in which the protozoa are particularly *Babesia bovis* or *Babesia bigemina*. Thus, the kit preferably includes a container comprising at least one peptide or at least one composition, according to the present invention, and instructions for use and/or at least a second container with another composition, such as an additional second biologically active compound. Also, it may include instrument or device of application.

The present invention is also illustrated by the following examples which, however, should not be construed as limiting the scope of protection of the invention. The characteristics described in the above specification and in the following examples may, separately and in any combination, serve as a basis for carrying out the present invention in its various possible embodiments.

EXAMPLES

Experimental Vaccine

Initially, it was carried out the obtaining of *Anaplasma marginale* corpuscles and vaccine antigens (membrane proteins from *A. marginale*) to be used in the immunization of cattle (experimental vaccine). From the sera of animals naturally infected by *A. marginale* and animals immunized with the experimental vaccine, subsequent proteomic analysis assays were carried out, resulting in the disclosure of peptide fragments, which were later evaluated in databases to identify potential epitopes (in silico analysis). Potential epitopes were classified according to the type of immune response (humoral and cellular) and then selected to make up the synthetic hybrid peptide sequences of the present invention.

Experimental Animals and Management

It was used crossbred male calves of Holstein breed (HPB×Gir). At regular 30-day intervals, shortly after birth and until the end of the experiment, the calves were treated with fluazuron acaricide to prevent a possible natural *B. microplus* infestation.

From the first days of life and until the end of the trial, the animals were artificially fed and received balanced feed for growing calves. During this period (4-5 months), the animals were also vaccinated against symptomatic carbuncle and foot-and-mouth disease and received deworming and ad libitum mineral salt. The rectal temperature of each calf was noted daily, in the morning and in the afternoon. Also, the animals were periodically tested for possible infection by *Babesia bovis, B. bigemine* and *Anaplasma marginale* (hematozoa research and detection of humoral immunities). For hematozoa research and determination of parasitemia, blood samples from experimental animals were obtained by puncture of the marginal ear vein. A hematozoa screening was performed on Giemsa-stained blood smears and the parasitemia was determined by counting the number of parasitized erythrocytes in 1000 red cells, with the aid of a reticulated and objective oil immersion eyepiece (1000×). Only negative animals were splenectomized.

Splenectomy

Calves between 4 and 5 months of age, negative for the above described hemoparasites, after receiving tranquilizer (2% xylazine hydrochloride) were subjected to shaving of the left lumbar region, from the 12th rib to the iliac tuberosity, with the threshold superior to the spine. Subsequently, local anesthesia was infiltrated continuously by administration of 2% xylocaine hydrochloride in inverted "L" in the region of the left paralumbar fossa. The animals on the operating table were kept in right lateral decubitus and the antisepsis of the operative field was performed with iodized alcohol. After placing the field cloths and using a scalpel, the skin was cut from the transverse apophysis of the first lumbar vertebra to approximately 2 cm from the caudal edge of the $13^{th}$ rib. In the background, with the aid of curved scissors, the oblique and transverse muscles of the abdomen were cut, and thus the peritoneum was also cut. After exposure of the cavity, the hand was introduced into the subcostal space next to the diaphragm, displacing the spleen of the latter and the rumen, by means of the manual serosa divulsion technique, which keeps the spleen adhered to the rumen. Thus, the splenic hilum was isolated, which was ligated with 000 cotton thread. After rigorous inspection of the ligated stump, the cavity was closed with a continuous scalloped-type suture with chromed catgut number 1, and fixed in the first suture plane, the peritoneum and transverse muscle and, in the background, the oblique muscles. Subsequently, horizontal "U" stitches with 000 cotton thread were applied to the skin. The postoperative period consisted of dressings with local application of 2% iodine tincture and antibiotic therapy based on penicillin and streptomycin for five consecutive days. Stitches were removed 10 days after surgery.

Experimental Infection

Experimental *Anaplasma marginale* infection was intravenously performed in splenectomized calves from four to five months of age. It was used to study pathogenic sample of *A. marginale* (Jaboticabal strain) as used in other studies (Barbosa da Silva, et al., 2014), Genbank access number {"type":"entrez-nucleotide","attrs":{"text":"KJ398398", "term_id":"612487314","term_text":"KJ398 398"}. This sample has been kept in splenectomized animals and dimethylsulfoxide (DMSO) at 10%, cryopreserved in liquid nitrogen at −196° C. After administration of the inoculum intravenously, parasitemia occurred around the twenty-third day with maximum parasitemia level of 20%. From this animal 200 to 300 mL of blood was collected and transfused into a second splenectomized calf. In this animal, the onset of infection and the maximum parasitemia level (40%) occurred around the third day to the seventh day after inoculation.

Screening for Anti-Parasite Antibodies by Indirect Immunofluorescence Reaction and ELISA Test To show possible exposure of experimental animals to *Babesia bovis, B. bigemina* and *Anaplasma marginale*, before splenectomy, blood serum samples from each calf were subjected to Indirect Immunofluorescence Reaction (RIFI) and ELISA test. In splenectomized calves, blood serum samples were collected 15 days before and 7 days after splenectomy. Only negative animals were used for experimental infection.

Indirect Immunofluorescence Reaction (IFR)

Antigen

The antigen used in the IFR consisted of intra-erythrocytic forms of *Babesia bovis, B. bigemina* and *Anaplasma marginale*, which were collected from splenectomized calves with high parasitemia degree (20%-40%). Blood parasitized by *Babesia* sp. and *Anaplasma marginale*, collected in an equal volume of Alsever solution, were washed in PBS pH 7.2 five consecutive times, eliminating the leukocyte porridge from the first wash. The sediment containing parasitized red blood cells was used to make thick smears on extra-thin and previously degreased microscopy slides. Methanol PA-fixed and Giemsa-stained smears revealed high concentration of parasites, that is, 20-30 parasitized red blood cells per microscopic field. Under these conditions, slide-prepared smears were dried at room temperature, wrapped in extra-thin toilet paper, and then separated into blocks containing five slides, which, when were properly labeled, were placed in a hermetically sealed container at −70° C. until the moment of use.

DESCRIPTION of the IFR Reaction

The technique used was the one established for *Babesia bovis* and *B. bigemina* according to the methodology of Machado et al., 1994. The slides prepared for IFR, as described above, were thawed, dried and the antigen-containing areas delimited in circles with the aid of red nail polish. Positive and negative control sera and those under study were diluted 1:80 in 0.85% saline and incubated with antigen in a humid chamber at 37° C. for 40 minutes. After this incubation period, the slides were subjected to three 5 minute washes each with PBS pH 7.2 and then dried and coated with conjugate (anti-bovine conjugate, Sigma), diluted as recommended by the manufacturer in PBS pH 7.2 containing 0.01% Evans Blue. The slides were again incubated in a humid chamber for 40 minutes at 37° C. There-after, they were subjected to three washes in PBS pH 7.2 and immersed in distilled water for 30 seconds. The slides were then dried and coverslipped using a glycerine solution buffered at a glycerin/carbonate bicarbonate buffer 0.5 M pH 9.5 of 9:1 ratio and then examined under a fluorescent light microscope.

Preparation of Antigens of *Anaplasma marginale*—Membrane Surface Proteins for Characterization of MSP5 and Performance of the ELISA Test Antigen Calves blood infected by *Anaplasma marginale* was collected in an equal volume of Alsever's solution, centrifuged to eliminate the plasma and the erythrocyte pellet washed three times with sterile 0.85% saline. After centrifugation, the pellet containing parasitized erythrocytes was diluted in 0.85% sterile saline at a 1:4 erythrocyte/diluent ratio. For lysis of parasitized erythrocytes, the technique described by Machado et al., 1994 was used. To this end, a 0.83% ammonium chloride solution was prepared and to nine volumes of this solution a volume of 0.17 M Tris buffer pH 7.65 was added. Next, this solution was heated in a water bath at 37° C. To each nine volumes of this solution was added a volume of erythrocyte suspension. The mixture was then incubated in a water bath at 37° C. for 3 minutes, observing visible hemolysis. Then, at the temperature of 5° C., the mixture was centrifuged at 2500×g for 15 minutes and the erythrocytic stroma-free sediment was washed in sterile 0.85% saline solution for three consecutive times. Thus, free *Anaplasma marginale* corpuscles were used for the preparation of crude soluble antigen. Part of this material was used, together with negative and positive sera (from animals naturally infected by *A. marginale*), in the proteomics analysis experiments described below. Part of the material was subjected to the sonication process (Sonicator Q55), with 100% power, pulse every 10 seconds for 5 minutes. The cell lysate was centrifuged at 1500×g (Sorvall Legend Mach 1.6R), during 15 minutes at 4° C. The obtained cell button contained total soluble antigen of *Anaplasma marginale*, and its protein concentration was measured by the method of Hartree (1972). The following, it was produced aliquots, it was lyophilized and kept at −70° C. until the moment of use. The same procedure was adopted to obtain surface antigens from normal red cells, that is, uninfected.

Description of the ELISA Test Reaction

After obtaining the antigen, protein content was determined by the bicinconic acid method using the BCA Reagent Kit (Pierce Chemical Company, UK) according to the manufacturer's recommendations. To the well of the flat bottom microplates (Nunclon™ Surface, Nunc. Denmark), it was added 100 µl of *A. marginale* protein diluted at 10 µg/mL reactivity concentration in 0.05 M sodium carbonate-bicarbonate buffer pH 9.6. After incubation, during 12 hours in a humid chamber at 4° C., the excess antigen was removed by three consecutive washes with PBS 0.01M pH 7.4 buffer containing 0.05% Tween 20 (PBS-Tween 20). Plates were blocked with PBS-Tween 20, plus 6% normal rabbit serum in a humidified chamber at 37° C. for 90 minutes. After further washing for removing the blocking agent, it was added in duplicate 100 µL of serum tests and positive and negative reference sera, diluted 1:400 in PBS-Tween 20. The microplates were incubated at 37° C. for 1 hour in a humid chamber and then washed as described above. One hundred microliters of alkaline phosphatase-coupled bovine conjugate (rabbit anti-bovine IgG, Sigma) diluted in PBS-Tween 20 was added to each well of the plate, followed by new incubation and washing as in the previous step. The substrate of alkaline phosphatase enzyme (paranitrophenyl phosphate—pNPP, Sigma) was added and the reaction incubated for 30 minutes at room temperature. After this time, the reaction was read on an ELISA microplate reader (Microplate Reader MRX TC Plus, Dynex Technology, USA) at a wavelength of 405 nm.

The immunological activity of each serum tested was calculated by determining the A/P value (sample versus positive), as described by Machado et al. (1997) and Andrade et al. (2004). Additionally, the optical density (OD) values of the sera were grouped into ELISA (NE) levels.

Proteomic Analysis

Two-Dimensional Electrophoresis

Samples of bovine sera of cattle animals crossbred of Holstein breed infected with highly virulent strain of *Anaplasma marginale* (Jaboticabal strain) from non-infected animals and animals infected with Jaboticabal strain and vaccinated (Experimental vaccine) as described above, were subjected to analysis by two-dimensional electrophoresis. According to such technique, the separation of proteins by their isoelectric point (first dimension) and molecular mass (second dimension) is allowed.

The bovine erythrocyte *Anaplasma marginale* membrane enriched sample was initially prepared for two-dimensional protein by precipitation electrophoresis using the commercial kit Readyprep 2-D Cleanup Kit, of Bio-Rad company, following manufacturer's instructions.

For separation in the first dimension by isoelectric point, precipitated proteins (100 µg) were dissolved in 125 µL rehydration solution containing 7 M urea, 2 M thiourea, 4% w/v CHAPS, 0.2% ampholyte 3/10 Bio-Rad v/v, 50 mM dithiothreitol (DTT) and 0.002% bromophenol blue. The solution containing the proteins was added to the isoelectric focusing strips of 7 cm from Bio-Rad for separation between pH 4 to pH 7 by rehydration for 16 hours at room temperature. Then the strips were placed on appropriate, targeted tray Protean i12 IEF System apparatus from Bio-Rad using the following schedule: 250 V for 20 minutes, gradually increasing to 4000 V for 2 hours and remaining at 4000 V to complete 14000 V-h. After focusing, the strips were equilibrated in equilibration buffer I (6 M urea, 2% SDS, 0.375 M Tris-HCl (pH 8.8), 20% glycerol and 25 nM DTT for 10 minutes stirring. The strips were then transferred to equilibration solution II (6 M urea, 2% SDS, 0.375 M Tris-HCl (pH 8.8), 20% glycerol). After this period, the strips were placed on top of 12.5% polyacrylamide gel in Bio-Rad Mini Protean kit for separation in the second dimension by molecular mass at a voltage of 140 V.

Two-dimensional electrophoresis analysis allowed the separation of anaplasma proteins by isoelectric point and molecular mass.

The electrophoresis gels were then stained by Commassie Blue or transferred to PVDF membrane for Western blotting analysis.

Western Blotting

The Western blotting assay allows the detection of one or two-dimensional gel-separated proteins and transferred to polymeric membranes to be specifically recognized by anti-protein antibodies of interest.

Following SDS-PAGE run, gel proteins were transferred by the semi-dry method (Trans-Blot SD semi-dry transfer cell, Bio-rad) to a PVDF membrane using the following conditions: 25 V, 0.5 A and 50 W for 50 minutes for one hour.

After transfer, the PVDF membranes were blocked in a solution of 5% skim milk in TBS for 16 hours at 4° C. and incubated under stirring for further 1 h with serum from infected and not protected animals or from immunized and protected animals, diluted 100× in the same solution at room temperature. The membranes were then washed 4× with TBS solution+1% Tween 20 and incubated for 1 hour with the second cattle anti-IgG mouse labeled with peroxidase. The membranes were again washed 4× with TBS+1% Tween 20 solution and developed with Bio-Rad Clarity Western ECL kit. The images were acquired with the aid of ChemiDoc MP Imaging System equipment from Bio-Rad.

The stained dots on the gels, corresponding to points revealed on the membranes, were cut and subjected to proteomic analysis to identify the proteins present on them.

Immunoprecipitation

Immunoprecipitation specifically separates lysate proteins that are recognized by antibodies of the infected animal. This methodology provides more accurate information about those proteins that actually induce an immune response in the infected animal.

Serum antibodies from unprotected infected cattle and from immunized and protected cattle are bound to a resin via protein A/G. Then, an *Anaplasma marginale* membrane lysate obtained from red blood cells of infected cattle is incubated with the antibody-bound resin. The resin is washed and then the proteins that bound the antibodies are removed. Through proteomic analysis by mass spectrometry the proteins with potential to induce the expression of protective antibodies were identified.

Antibodies from sera from infected and diseased, immunized and protected cattle or from healthy cattle were coupled to the A/G protein-bound resin and the immunoprecipitation of *A. marginale* proteins recognized by unprotected and infected bovine serum and immunized and protected bovine serum was performed using the Pierce Crosslink IP kit from Thermo Scientific following manufacturer's instructions. The sera used consisted of sera pool from several animals in the same condition. The solutions containing the immunoprecipitated proteins were subjected to proteomic analysis to identify the proteins recognized by the antibody.

Proteomic Analysis

Shotgun-type proteomic analysis consists of identifying the set of proteins in a given sample. In this step, samples in the gel spot or solution obtained by immunoprecipitation elution are analyzed by mass spectrometry. To this end, the proteins of the samples undergo a process of: (1) reducing where disulfide bridges break, (2) alkylation where the —SH groups are alkylated to prevent formation of the disulfide bridges, (3) digestion with trypsin enzyme and (4) desalination. The samples are then analyzed on the mass spectrometer. The identification of proteins is made by analyzing the data with the aid of Mascot program that makes a search of the peptides identified from a database of protein sequences of *Anaplasma*.

Trypsin in Gel Digestion

The trypsin in gel digestion steps were performed according to Hanna et al. (2000), where the spots of interest of the gel were cut from two-dimensional SDS-polyacrylamide gels (about 1 mm×5 mm) and placed in 1500 μL centrifuge tubes previously washed with absolute ethanol and dried in greenhouse.

Each gel spot was incubated in 50% methanol and 5% acetic acid solution for 3 hours to remove SDS (sodium dodecyl sulfate). After this time the solution was removed and the gel was dehydrated with 100% acetonitrile for 5 minutes twice; the gel was then dried by vacuum centrifugation (Speed Vac-SC210A Savant) for 3 minutes and after drying was added a 10 mM DTT solution (dithiothreitol) in ammonium bicarbonate 100 mM (30 μl) to reduce disulfide bridges for a period of 30 minutes. After rapid centrifugation, the DTT solution was removed and 30 μl of 50 mM iodoacetamide in 100 mM ammonium bicarbonate was added for 30 minutes for alkylation of the cysteine side chain SH groups. After rapid centrifugation, the supernatant was removed and the gel was washed with 100 mM ammonium bicarbonate solution and again dehydrated with 100% acetonitrile for 5 minutes, rehydrated with 100 mM ammonium bicarbonate for 10 minutes and dehydrated with 100% acetonitrile for 5 minutes twice.

After drying the gel by vacuum centrifugation for three minutes, 30 μL trypsin 50 g/mL (Sigma) solution were added prepared in ice cold 50 mM ammonium bicarbonate. Incubation was performed for 30 minutes in an ice bath. After this step, the trypsin solution was removed (supernatant) and the gel fragment was added 20 μL of 50 mM ammonium bicarbonate and incubation was continued for 16 hours at 37° C.

Trypsin Digestion in Solution

To the lysed samples were added 5 μL of 1 M DTT to reduce disulfide bridges, and they were incubated for 1.5 hours at room temperature. After incubation with DTT, 20 μl of iodoacetamide was added for alkylation of cysteines for 1 hour in the dark at room temperature. To consume unreacted iodoacetamide, 20 μL of DTT was added and the samples were incubated for an additional 1 hour. After incubation, 775 μl Milli-Q water and 2 μl trypsin (Sigma) were added in sufficient amount to give a protein ratio of 1:50, and the samples were then incubated at 37° C. overnight. The next day, the reaction was stopped by adding 2 μL of 100% acetic acid.

Desalination of Samples

The samples were desalted using Sep-Pak Light tC18 solid phase extraction columns (Waters Corporation, United States). Initially, the columns were conditioned with 2 mL methanol, followed by 2 mL of 0.1% trifluoroacetic acid (TFA) and 50% acetonitrile (ACN) and 1 mL of 0.1% TFA. After conditioning, the samples were loaded with 1 mL of 0.1% TFA twice, washed with 0.1% TFA, and eluted from the column with 2 mL of 0.1% TFA and 50% ACN slowly transferring to a new 2 mL centrifuge tube. Then, the Sep-Pak was washed with 2 mL of 100% ACN.

The samples were dried and concentrated in Speed-Vac (RVC 2-18, CHRIST, Analytical). After complete drying, the samples were resuspended in 20 μL of 0.1% formic acid and centrifuged at 1000 rpm for 5 minutes for analysis in the mass spectrometer.

Mass Spectrometer Analysis

The samples were analyzed on the LTQ Orbitrap Velos mass spectrometer (Thermo Scientific, United States)

coupled to the EASY-nLC nano-flow liquid chromatograph (Thermo Scientific, United States). The peptides were separated by a 120 minute gradient program as follows: 5-40% solvent B (90% acetonitrile in 0.1% formic acid) for 90 minutes followed by 40-90% solvent B for 20 minutes in the 200 nL/min stream using a 5 cm packed pre-column having 5 cm of 10 µm C18 beads (Jupiter, Phenomenex) in an ID 100 µm×OD 360 µm capillary and a frit-tip analytical column packaged with 15 cm of 5 cm B18 beads (Aqua, Phenomenex) in a ID 75 µm×OD 360 µm capillary.

The mass spectrometer was operated in Data Dependent Acquisition (DDA) mode, wherein the 10 most intense ions from each sample were selected for linear ion trap fragmentation using dissociation-induced collision fragmentation dissociation (CID) in MS/MS. Data acquisition was controlled by the Xcalibur 1.4 program (Thermo Scientific). The conditions of analysis were: 2.3 kV nano-electrospray capillary voltage, 250° C. source temperature, 100 ms ion-trap injection time and 1000 ms FT-MS with a resolution of 60,000 in m/z 300-1800. The dynamic exclusion time has been set to 70 seconds. Mass data files (.raw) were converted to .mgf using the MS Convert program (v.3.0.4445, ProteoWizard, SourceForge) and analyzed in Mascot (v.2.4, Matrix Science Ltd, Boston, Mass., USA). The proteins were identified by searching MS and MS/MS data in *Anaplasma* sp. database downloaded from Uniprot. Trypsin was defined for enzyme specificity with a maximum of two miss cleavages, the mass tolerance of precursor ions was set to 0.17. In the search for MS/MS spectra, carbamidomethylation of cysteine residues was determined as fixed modification, while methionine oxidation and N-terminal protein acetylation were defined as variable modifications.

Each spot was treated and analyzed using an Orbitrap-type mass spectrometer coupled with a nano-chromatograph, which allowed the identification of proteins in that particular spot. The Table 1A-M shows the proteins identified by proteome analysis of each spot corresponding to the spot on the PVDF membrane recognized by sera from immunized and protected animals identified by the analysis by Western blotting.

TABLE 1

Proteins recognized in gel spots by vaccinated ox serum (comprising antibodies) in proteomic analysis Table 1A-Spot 1

50S ribosomal protein L7/L12 OS = *Anaplasma centrale* (strain Israel)
ATP synthase F1, gamma subunit OS = *Anaplasma phagocytophilum* (strain HZ)
Citrate synthase (Fragment) OS = uncultured *Bartonella* sp.
DNA-directed RNA polymerase subunit alpha OS = *Anaplasma marginale* (strain St. Maries)
Lon protease OS = *Anaplasma centrale* (strain Israel)
Major surface protein 2 (Fragment) OS = *Anaplasma marginale*
Major surface protein 2 (Fragment) OS = *Anaplasma marginale*
Membrane protein OS = *Anaplasma marginale* str. Gypsy Plains
Msp2 (Fragment) OS = *Anaplasma marginale*
OMP10 (Fragment) OS = *Anaplasma marginale* (strain St. Maries)
OMP14 (Fragment) OS = *Anaplasma marginale* (strain St. Maries)
OMP4 OS = *Anaplasma marginale* (strain Florida)
OMP8 OS = *Anaplasma marginale* (strain St. Maries)
OMP9 OS = *Anaplasma marginale* (strain Florida)
Outer membrane protein 14 OS = *Anaplasma marginale*
Outer membrane protein 8 OS = *Anaplasma marginale*
Phosphoribosylamine-glycine ligase OS = *Anaplasma centrale* (strain Israel)
Putative isomerase OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Uncharacterized protein OS = *Anaplasma marginale* str. Gypsy Plains
Uncharacterized protein OS = *Anaplasma phagocytophilum* str.

Table 1 B-Spot 4

1-deoxy-D-xylulose 5-phosphate reductoisomerase OS = *A. marginale* (strain St. Maries)
BoIA-like protein OS = *Anaplasma centrale* (strain Israel)
DNA-directed RNA polymerase subunit alpha OS = *Anaplasma marginale* (strain St. Maries)
Immunogenic protein OS = *Anaplasma phagocytophilum* (strain HZ)
Iron binding protein FbpA OS = *Anaplasma marginale* (strain St. Maries)
Major surface protein 2 (Fragment) OS = *Anaplasma marginale*
Major surface protein 2 OS = *Anaplasma marginale*
Major surface protein 2 OS = *Anaplasma ovis*
Major surface protein 2 variant 9H1 (Fragment) OS = *Anaplasma marginale*
Major surface protein 3 OS = *Anaplasma centrale* (strain Israel)
Major surface protein 3 OS = *Anaplasma marginale*
Msp2 (Fragment) OS = *Anaplasma marginale*
OMP14 (Fragment) OS = *Anaplasma marginale* (strain St. Maries)
OMP7 (Fragment) OS = *Anaplasma marginale* (strain St. Maries)
OMP9 OS = *Anaplasma marginale* (strain Florida)
Putative serine protease OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Ribosomal RNA small subunit methyltransferase A OS = *A. phagocytophilum* (strain HZ)
Type IV secretion system protein VirB10 OS = *Anaplasma centrale* (strain Israel)

Table 1C-Spot 5

2-oxoglutarate dehydrogenase E1 component (Fragment) OS = *A. phagocytophilum*
AnkA OS = *Anaplasma phagocytophilum*
BoIA-like protein OS = *Anaplasma centrale* (strain Israel)

TABLE 1-continued

Proteins recognized in gel spots by vaccinated ox serum
(comprising antibodies) in proteomic analysis DNA-directed RNA polymerase subunit alpha OS = *A. phagocytophilum* (strain HZ)
DNA-directed RNA polymerase subunit beta OS = *Wolbachia pipientis*
MSP2 family outer membrane protein OS = *Anaplasma phagocytophilum* str.
Major surface protein 2 (Fragment) OS = *Anaplasma marginale*
Major surface protein 2 OS = *Anaplasma marginale*
Major surface protein 2 variant 9H1 (Fragment) OS = *Anaplasma marginale*
Msp2 (Fragment) OS = *Anaplasma marginale*
Putative NADH-quinone oxidoreductase, degenerate OS = *A. phagocytophilum* (strain HZ)
Putative serine protease OS = *Anaplasma centrale* (strain Israel)
Putative uncharacterized protein OS = *Anaplasma centrale* (strain Israel)
Ribosomal RNA small subunit methyltransferase A OS = *A. phagocytophilum* (strain HZ)
Succinyl-CoA ligase [ADP-forming] subunit beta OS = *Anaplasma centrale* (strain Israel)
Type IV secretion system protein VirB10 OS = *Anaplasma centrale* (strain Israel)
Uncharacterized protein OS = *Anaplasma phagocytophilum* (strain HZ)
Uncharacterized protein OS = *Anaplasma phagocytophilum* str. CRT38
Table 1D-Spot 6

3-hydroxyacyl-CoA dehydrogenase OS = *Anaplasma marginale* str. Gypsy Plains
Citrate synthase OS = *Anaplasma marginale* (strain St. Maries)
DNA-directed RNA polymerase subunit alpha OS = *Anaplasma centrale* (strain Israel)
DNA-directed RNA polymerase subunit beta OS = *Anaplasma centrale* (strain Israel)
Elongation factor Tu OS = *Anaplasma marginale* (strain St. Maries)
Fumarate hydratase class II OS = *Anaplasma centrale* (strain Israel)
GMP synthase [glutamine-hydrolyzing] OS = *Anaplasma marginale* (strain St. Maries)
Major surface protein 2 (Fragment) OS = *Anaplasma marginale*
Major surface protein 2 variant 9H1 (Fragment) OS = *Anaplasma marginale*
Major surface protein 3 (Fragment) OS = *Anaplasma marginale*
Major surface protein 3 OS = *Anaplasma centrale* (strain Israel)
Major surface protein 3 OS = *Anaplasma marginale*
Msp2 (Fragment) OS = *Anaplasma marginale*
OMP8 OS = *Anaplasma marginale* (strain St. Maries)
Outer membrane protein 8 OS = *Anaplasma marginale*
Peptide chain release factor 1 OS = *Anaplasma centrale* (strain Israel)
Phosphoribosylamine-glycine ligase OS = *Anaplasma marginale* (strain St. Maries)
Probable cytosol aminopeptidase OS = *Anaplasma centrale* (strain Israel) GN = pepA
Proline-tRNA ligase OS = *Anaplasma marginale* str. Gypsy Plains
Putative dihydrolipoamide acetyltransferase OS = *Anaplasma centrale* (strain Israel)
Putative glutamate synthase OS = *Anaplasma centrale* (strain Israel) GN = ACIS_00837
Putative serine protease OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Ribosomal RNA small subunit methyltransferase A OS = *A. phagocytophilum* (strain HZ)
Serine hydroxymethyltransferase OS = *Anaplasma centrale* (strain Israel)
Succinyl-CoA ligase [ADP-forming] subunit beta OS = *Anaplasma centrale* (strain Israel)
Transcription termination factor Rho OS = *Anaplasma centrale* (strain Israel)
Type IV secretion system protein VirB10 OS = *Anaplasma centrale* (strain Israel)
Uncharacterized protein OS = *Anaplasma marginale* str. Gypsy Plains
Uncharacterized protein OS = *Anaplasma phagocytophilum* (strain HZ)
tRNA (guanine-N(1)-)-methyltransferase OS = *Anaplasma centrale* (strain Israel)
Table 1E-Spot 7

Aspartate aminotransferase OS = *Anaplasma centrale* (strain Israel)
DNA polymerase III, delta subunit OS = *Anaplasma phagocytophilum* (strain HZ)
DNA-directed RNA polymerase subunit alpha OS = *Anaplasma centrale* (strain Israel)
DNA-directed RNA polymerase subunit beta OS = *Wolbachia pipientis*
Iron binding protein FbpA OS = *Anaplasma marginale* (strain St. Maries)
MSP2 family outer membrane protein OS = *Anaplasma phagocytophilum* str. CRT38
Major surface protein 2 (Fragment) OS = *Anaplasma marginale*
Major surface protein 2 (Fragment) OS = *Anaplasma marginale*
Major surface protein 2 (MSP2) OS = *Anaplasma marginale* (strain Florida)
Major surface protein 2 OS = *Anaplasma marginale*
Major surface protein 2 OS = *Anaplasma marginale*
Malate dehydrogenase OS = *Anaplasma marginale* str. Gypsy Plains
Msp2 (Fragment) OS = *Anaplasma marginale*
OMP5 OS = *Anaplasma marginale* (strain Florida)
OMP9 OS = *Anaplasma marginale* (strain Florida)
Outer membrane protein 7 OS = *Anaplasma marginale* (strain St. Maries)
Primosomal protein N~OS = *Anaplasma centrale* (strain Israel)
Putative uncharacterized protein OS = *Anaplasma marginale* (strain St. Maries)
Transcription termination/antitermination protein NusA OS = *A. phagocytophilum* (st HZ)
Type IV secretion system protein VirB10 OS = *Anaplasma centrale* (strain Israel)
Uncharacterized protein OS = *Anaplasma phagocytophilum* (strain HZ)
Table 1F-Spot 8

Adenylosuccinate synthetase OS = *Anaplasma centrale* (strain Israel)
Immunogenic protein OS = *Anaplasma phagocytophilum* (strain HZ)
Major surface protein 2 (Fragment) OS = *Anaplasma marginale*

TABLE 1-continued

Proteins recognized in gel spots by vaccinated ox serum
(comprising antibodies) in proteomic analysis Major surface protein 2 OS = *Anaplasma marginale*
Major surface protein 2 variant 9H1 (Fragment) OS = *Anaplasma marginale*
Major surface protein 2 variant 9H1/G11/E6F7 (Fragment) OS = *Anaplasma marginale*
Major surface protein 3 (Fragment) OS = *Anaplasma marginale*
Malate dehydrogenase OS = *Anaplasma marginale* str. Gypsy Plains
Msp2 (Fragment) OS = *Anaplasma marginale*
OMP5 OS = *Anaplasma marginale* (strain Florida)
OMP9 OS = *Anaplasma marginale* (strain Florida)
Outer membrane protein 7 OS = *Anaplasma marginale* (strain St. Maries)
Putative uncharacterized protein OS = *Anaplasma centrale* (strain Israel)
Putative uncharacterized protein OS = *Anaplasma marginale* (strain St. Maries)
Uncharacterized protein OS = *Anaplasma phagocytophilum* (strain HZ)
Table 1G-Spot 9

Major surface protein 2 (Fragment) OS = *Anaplasma marginale*
Major surface protein 2 (Fragment) OS = *Anaplasma marginale*
Major surface protein 2 (Fragment) OS = *Anaplasma phagocytophilum*
Major surface protein 2 (MSP2) OS = *Anaplasma marginale* (strain Florida)
Major surface protein 2 OS = *Anaplasma marginale*
Major surface protein 2 OS = *Anaplasma marginale*
Major surface protein 2 hypervariable region (Fragment) OS = *Anaplasma marginale*
Major surface protein 2 variable region (Fragment) OS = *Anaplasma phagocytophilum*
Major surface protein 2 variant 9H1/G11/E6F7 (Fragment) OS = *Anaplasma marginale*
Major surface protein 3 OS = *Anaplasma centrale* (strain Israel)
Major surface protein 3 OS = *Anaplasma marginale*
Malate dehydrogenase OS = *Anaplasma marginale* str. Gypsy Plains
Msp2 (Fragment) OS = *Anaplasma marginale*
OMP13 OS = *Anaplasma marginale* (strain St. Maries)
OMP5 OS = *Anaplasma marginale* (strain Florida)
OMP7 (Fragment) OS = *Anaplasma marginale* (strain St. Maries)
Outer membrane protein 4 OS = *Anaplasma marginale*
Putative uncharacterized protein OS = *Anaplasma centrale* (strain Israel)
Putative uncharacterized protein OS = *Anaplasma marginale* (strain St. Maries)
Table 1H-Spot 10

30S ribosomal protein S2 OS = *Anaplasma phagocytophilum* (strain HZ)
AnkA OS = *Anaplasma phagocytophilum*
Cell division protein ftsA OS = *Anaplasma phagocytophilum* (strain HZ)
Immunogenic protein OS = *Anaplasma phagocytophilum* (strain HZ)
Iron binding protein FbpA OS = *Anaplasma marginale* (strain St. Maries)
Major surface protein 2 (Fragment) OS = *Anaplasma marginale*
Major surface protein 4 (Fragment) OS = *Anaplasma marginale*
Malate dehydrogenase OS = *Anaplasma marginale* str. Gypsy Plains
Msp2 (Fragment) OS = *Anaplasma marginale*
Proline-tRNA ligase OS = *Anaplasma marginale* (strain St. Maries)
Putative uncharacterized protein OS = *Anaplasma centrale* (strain Israel)
Putative uncharacterized protein OS = *Anaplasma marginale* (strain St. Maries)
Succinyl-CoA ligase [ADP-forming] subunit alpha OS = *Anaplasma centrale* (strain Israel)
Table 1I-Spot 11

30S ribosomal protein S2 OS = *Anaplasma phagocytophilum* (strain HZ)
50S ribosomal protein L7/L12 OS = *Anaplasma centrale* (strain Israel)
CvpA family protein OS = *Anaplasma phagocytophilum* (strain HZ)
Immunogenic protein OS = *Anaplasma phagocytophilum* (strain HZ)
Major surface protein 2 (Fragment) OS = *Anaplasma marginale*
Major surface protein 3 (Fragment) OS = *Anaplasma marginale*
OMP1 OS = *Anaplasma marginale* (strain Florida)
OMP4 OS = *Anaplasma marginale* (strain Florida)
Outer membrane protein 4 OS = *Anaplasma marginale*
Putative 3-phosphoshikimate 1-carboxyvinyltransferase OS = *A. phagocytophilum* (strain
Putative uncharacterized protein OS = *Anaplasma marginale* (strain St. Maries)
Quinone oxidoreductase OS = *Anaplasma centrale* (strain Israel) GN = qor PE = 4 SV = 1
Succinyl-CoA ligase [ADP-forming] subunit alpha OS = *Anaplasma centrale* (strain Israel)
Uncharacterized protein OS = *Anaplasma marginale* str. Gypsy Plains
Uncharacterized protein OS = *Anaplasma phagocytophilum* str. CR138
Table 1J-Spot 14

60 kDa chaperonin (Fragment) OS = *Anaplasma phagocytophilum*
ATP synthase subunit beta OS = *Anaplasma marginale* (strain St. Maries)
Ana29 OS = *Anaplasma marginale* (strain St. Maries)
Aspartyl/glutamyl-tRNA(Asn/Gln) amidotransferase subunit B OS = *A. centrale* (str Israel)
Dihydrolipoamide acetyltransferase component OS = *A. marginale* (strain St. Maries)
Elongation factor Tu OS = *Anaplasma centrale* (strain Israel)
Major surface protein 2 (Fragment) OS = *Anaplasma marginale*
Major surface protein 2 variant 9H1 (Fragment) OS = *Anaplasma marginale*
Msp1B OS = *Anaplasma marginale*
P44-new outer membrane protein OS = *Anaplasma phagocytophilum* str. CRT38

TABLE 1-continued

Proteins recognized in gel spots by vaccinated ox serum
(comprising antibodies) in proteomic analysis Peptidase M16 OS = *Anaplasma marginale* str. Dawn
PmbA protein OS = *Anaplasma marginale* (strain St. Maries)
Probable cytosol aminopeptidase OS = *Anaplasma marginale* (strain St. Maries)
Putative serine protease OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Succinyl-CoA ligase [ADP-forming] subunit beta OS = *Anaplasma centrale* (strain Israel)
Uncharacterized protein OS = *Anaplasma phagocytophilum* str. HZ2
VirB10 protein OS = *Anaplasma marginale* (strain St. Maries)
Table 1K-Spot 15

50S ribosomal protein L7/L12 OS = *Anaplasma centrale* (strain Israel)
Adenylosuccinate synthetase OS = *Anaplasma centrale* (strain Israel)
Adenylosuccinate synthetase OS = *Anaplasma marginale* (strain St. Maries)
AnkA OS = *Anaplasma phagocytophilum*
DNA polymerase III subunit beta OS = *Anaplasma centrale* (strain Israel)
Elongation factor Tu OS = *Anaplasma marginale* (strain St. Maries)
Immunogenic protein OS = *Anaplasma phagocytophilum* (strain HZ)
Major surface protein 2 (Fragment) OS = *Anaplasma marginale*
Major surface protein 2 variant 9H1 (Fragment) OS = *Anaplasma marginale*
Major surface protein 3 (Fragment) OS = *Anaplasma marginale*
Major surface protein 3 (MSP3) OS = *Anaplasma marginale* (strain Florida)
Major surface protein 3 OS = *Anaplasma centrale* (strain Israel)
Msp2 (Fragment) OS = *Anaplasma marginale*
P44-new outer membrane protein OS = *Anaplasma phagocytophilum* str. CR138
Peptidase M16 OS = *Anaplasma marginale* str. Dawn
Phosphoribosylamine-glycine ligase OS = *Anaplasma centrale* (strain Israel)
PmbA protein OS = *Anaplasma marginale* (strain St. Maries)
Probable cytosol aminopeptidase OS = *Anaplasma marginale* (strain St. Maries)
Protease DO family protein OS = *Anaplasma phagocytophilum* (strain HZ)
Putative dihydrolipoamide acetyltransferase OS = *Anaplasma centrale* (strain Israel)
Putative serine protease OS = *Anaplasma centrale* (strain Israel)
Putative uncharacterized protein OS = *Anaplasma marginale* (strain St. Maries)
Succinyl-CoA ligase [ADP-forming] subunit beta OS = *A. marginale* (strain St. Maries)
Type IV secretion system protein VirB10 OS = *Anaplasma centrale* (strain Israel)
Uncharacterized protein OS = *Anaplasma phagocytophilum* str. HZ2
Uncharacterized protein OS = *Anaplasma phagocytophilum* str. HZ2
p44 outer surface protein (Fragment) OS = *Anaplasma phagocytophilum*
Table 1L-Spot 16

2-oxoglutarate dehydrogenase E1 component (Fragment) OS = *A. phagocytophilum*
Adenylosuccinate synthetase OS = *Anaplasma marginale* (strain St. Maries)
AnkA OS = *Anaplasma phagocytophilum*
Elongation factor Tu OS = *Anaplasma marginale* (strain St. Maries)
Major surface protein 1b (Fragment) OS = *Anaplasma marginale*
Major surface protein 2 (Fragment) OS = *Anaplasma marginale*
Major surface protein 3 (Fragment) OS = *Anaplasma marginale*
Major surface protein 3 (MSP3) OS = *Anaplasma marginale* (strain Florida)
Major surface protein 3 OS = *Anaplasma centrale* (strain Israel)
Msp2 (Fragment) OS = *Anaplasma marginale*
Peptidase M16 OS = *Anaplasma marginale* str. Dawn
Peptidase pmbA OS = *Anaplasma centrale* (strain Israel)
Peptide chain release factor 1 OS = *Anaplasma centrale* (strain Israel)
Phosphoribosylamine-glycine ligase OS = *Anaplasma centrale* (strain Israel)
Probable cytosol aminopeptidase OS = *Anaplasma marginale* (strain St. Maries)
Protease DO family protein OS = *Anaplasma phagocytophilum* (strain HZ)
Putative dihydrolipoamide acetyltransferase OS = *Anaplasma centrale* (strain Israel)
Putative serine protease OS = *Anaplasma centrale* (strain Israel)
Putative transcriptional regulator OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Succinyl-CoA ligase [ADP-forming] subunit beta OS = *A. marginale* (strain St. Maries)
Type IV secretion system protein VirB10 OS = *Anaplasma centrale* (strain Israel)
Uncharacterized protein OS = *Anaplasma phagocytophilum* str. CRT38
tRNA (guanine-N(1)-)-methyltransferase OS = *Anaplasma centrale* (strain Israel)
Table 1M-Spot 17

30S ribosomal protein S2 OS = *Anaplasma centrale* (strain Israel)
ATP synthase subunit beta OS = *Anaplasma centrale* (strain Israel)
Aminomethyl transferase family protein OS = *Anaplasma phagocytophilum* (strain HZ)
AnkA OS = *Anaplasma phagocytophilum*
Citrate synthase OS = *Anaplasma marginale* (strain St. Maries)
CypA family protein OS = *Anaplasma phagocytophilum* (strain HZ)
DNA-directed RNA polymerase subunit alpha OS = *Anaplasma centrale* (strain Israel)
DNA-directed RNA polymerase subunit beta OS = *Anaplasma centrale* (strain Israel
Dihydrolipoyl dehydrogenase OS = *Anaplasma marginale* (strain St. Maries)
Elongation factor Tu OS = *Anaplasma centrale* (strain Israel)

TABLE 1-continued

Proteins recognized in gel spots by vaccinated ox serum (comprising antibodies) in proteomic analysis GMP synthase [glutamine-hydrolyzing] OS = *Anaplasma marginale* (strain St. Maries)
Glutamyl-tRNA(Gln) amidotransferase subunit A OS = *Anaplasma centrale* (strain Israel)
Immunogenic protein OS = *Anaplasma phagocytophilum* (strain HZ)
Major surface protein 1 beta 2 OS = *Anaplasma marginale*
Major surface protein 2 (Fragment) OS = *Anaplasma marginale*
Major surface protein 2 variant 9H1 (Fragment) OS = *Anaplasma marginale*
Major surface protein 3 (Fragment) OS = *Anaplasma marginale*
Major surface protein 3 OS = *Anaplasma marginale*
Msp2 (Fragment) OS = *Anaplasma marginale*
Phosphoribosylamine-glycine ligase OS = *Anaplasma marginale* (strain St. Maries)
PmbA protein OS = *Anaplasma marginale* (strain St. Maries)
Probable cytosol aminopeptidase OS = *Anaplasma marginale* (strain St. Maries)
Probable cytosol aminopeptidase OS = *Anaplasma marginale*
Putative DNA gyrase control protein TldD OS = *Anaplasma centrale* (strain Israel)
Putative dihydrolipoamide acetyltransferase OS = *Anaplasma centrale* (strain Israel)
Putative serine protease OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Putative uncharacterized protein pepl OS = *Anaplasma marginale* (strain St. Maries)
Ribosomal RNA small subunit methyltransferase A OS = *A. phagocytophilum* (strain HZ)
Serine hydroxymethyltransferase OS = *Anaplasma centrale* (strain Israel)
Succinyl-CoA ligase [ADP-forming] subunit beta OS = *Anaplasma centrale* (strain Israel)
Trigger factor OS = *Anaplasma marginale* (strain St. Maries)
Trigger factor OS = *Anaplasma marginale* str. Gypsy Plains
Uncharacterized protein OS = *Anaplasma phagocytophilum* str. JM
p44 outer surface protein (Fragment) OS = *Anaplasma phagocytophilum*
tRNA (guanine-N(1)-)-methyltransferase OS = *Anaplasma centrale* (strain Israel)
Table 1N-Spot 18

3-hydroxyacyl-CoA dehydrogenase OS = *Anaplasma marginale* str. Gypsy Plains
Citrate synthase OS = *Anaplasma marginale* (strain St. Maries)
DNA-directed RNA polymerase subunit alpha OS = *Anaplasma centrale* (strain Israel)
DNA-directed RNA polymerase subunit beta OS = *Anaplasma centrale* (strain Israel)
Elongation factor Tu OS = *Anaplasma marginale* (strain St. Maries)
Fumarate hydratase class II OS = *Anaplasma centrale* (strain Israel)
GMP synthase [glutamine-hydrolyzing] OS = *Anaplasma marginale* (strain St. Maries)
Major surface protein 2 (Fragment) OS = *Anaplasma marginale*
Major surface protein 2 variant 9H1 (Fragment) OS = *Anaplasma marginale*
Major surface protein 3 (Fragment) OS = *Anaplasma marginale*
Major surface protein 3 OS = *Anaplasma centrale* (strain Israel)
Major surface protein 3 OS = *Anaplasma marginale*
Msp2 (Fragment) OS = *Anaplasma marginale*
OMP8 OS = *Anaplasma marginale* (strain St. Maries)
Outer membrane protein 8 OS = *Anaplasma marginale*
Peptide chain release factor 1 OS = *Anaplasma centrale* (strain Israel)
Phosphoribosylamine-glycine ligase OS = *Anaplasma marginale* (strain St. Maries)
Probable cytosol aminopeptidase OS = *Anaplasma centrale* (strain Israel)
Proline-tRNA ligase OS = *Anaplasma marginale* str. Gypsy Plains
Putative dihydrolipoamide acetyltransferase OS = *Anaplasma centrale* (strain Israel)
Putative glutamate synthase OS = *Anaplasma centrale* (strain Israel)
Putative serine protease OS = *Anaplasma centrale* (strain Israel)
Putative uncharacterized protein OS = *Anaplasma centrale* (strain Israel)
Putative uncharacterized protein OS = *Anaplasma marginale* (strain St. Maries)
Ribosomal RNA small subunit methyltransferase A OS = *A. phagocytophilum* (strain HZ)
Serine hydroxymethyltransferase OS = *Anaplasma centrale* (strain Israel)
Succinyl-CoA ligase [ADP-forming] subunit beta OS = *Anaplasma centrale* (strain Israel)
Transcription termination factor Rho OS = *Anaplasma centrale* (strain Israel)
Type IV secretion system protein VirB10 OS = *Anaplasma centrale* (strain Israel)
Uncharacterized protein OS = *Anaplasma marginale* str. Gypsy Plains
Uncharacterized protein OS = *Anaplasma phagocytophilum* (strain HZ)
tRNA (guanine-N(1)-)-methyltransferase OS = *Anaplasma centrale* (strain Israel)

Rational in Silico Screening Strategy

Data from proteomic analysis of serum from *A. marginale* infected and vaccinated cattle (experimental vaccine) (vaccinated group) were used to direct the in silico screening of peptide fragments with immunogenic potential. However, proteomic analysis allowed the identification of antibody-recognized protein fragments in 3 animal groups: infected and vaccinated animals (vaccinated group), infected animals (positive group) and uninfected animals (negative group).

153 proteins were identified in the group of infected and vaccinated animals (vaccinated group) and among these proteins were 80 different protein fragments (some smaller fragments were contained in the larger fragments), which were separated according to their respective protein families. It is noteworthy that 50% of the identified fragments in the serum of vaccinated animals belonged to the major surface proteins MSP: MSP1a, MPS2 and MPS3, and outer membrane OMP: OMP7 and OMP8 from *A. marginale*.

The search for epitopes of *A. marginale*, with published immunogenicity experimental data (lymphocyte proliferation assays of TCD4 and IgG2 antibody production) was performed on the IEDB free access database (Immune Epitope Database and Analysis Resource; Vita et al., 2014), which has a significant number of citations in scientific articles.

The search conditions were as follows: ruminant host; positive assays for T lymphocyte and B lymphocyte mediated response; antigens available for *Anaplasma marginale* contemplating the MSP protein family (MSP1a, MSP2, MSP3) and virulence factors (VirB9, VirB10). Virulence factors are secreted by a rickettsia complex called T4SS, which promotes host cell invasion and intracellular survival of rickettsia. Tests performed on cattle have shown that VirB9 and VirB10 factors stimulate both cellular (T lymphocyte proliferation) and humoral (IgG antibody production) immune response (Lopez et al., 2007; Araújo et al., 2008; Morse et al., 2012a; Morse et al., 2012b). The OMP7 and OMP8 proteins are not available in the IEDB database and, therefore, the search for potential epitopes for these proteins considered the immunogenicity data published in scientific articles. Such proteins have been described as antigenic and stimulate humoral response in cattle (response involving antibody production against these proteins) (Junior et al., 2010; Crosby et al., 2015).

Screening in the database resulted in 139 potential epitopes, with experimental data available for previously selected antigens (MSP1a, MSP2, MSP3, VirB9 and VirB10). According to the cellular and humoral responses that each epitope presented in immunogenicity assays with BALB/c mice and/or bovine, the most promising epitopes were selected.

The proteins MSP1a, MSP2 and MSP3, identified in the experimental vaccine (proteomic analysis), presented epitopes with experimental data deposited in the IEDB database. The MSP1a surface protein has adhesion function in the bovine erythrocyte and stimulates both humoral and cellular immune response (Garcia-Garcia et al., 2004; Santos et al., 2013; McGuire et al., 1994). MSP2 and MSP3 are the prevalent membrane surface proteins in the *A. marginale* rickettsia membrane and stimulate the humoral response. However, as they have hypervariable regions (mutations), the protection given is not effective (Abbott et al., 2004; Abbott et al., 2005; Noh et al., 2010). It is desirable that the two response subtypes, humoral and cellular, are triggered for greater protection against rickettsia.

As a result of the screening, from the inventors' guidance, 19 peptide fragments were obtained according to SEQ ID NO: 1 to 19. The combination of epitopes separated by a spacer agent in the same sequence, according to the hybrid peptides disclosed by the present invention seeks an improved action and response, and may also lead to synergism. The spacer agent used also has a peptide nature (3 to 5 glycine residues, Gly or G). Glycine is an unsubstituted amino acid (side chain=H) and therefore, does not interfere with the electronic properties, nor the flexibility (conformational arrangement) of the major peptide chain of hybrid fragments.

Hybrid peptide design was also considered as the preferred size to be presented as epitopes via the major histocompatibility complex (MHC II) (Kim, Sette, Peters, 2011).

It should be noted that the rational analysis, even if conducted by the inventor in order to enhance the chances of success in achieving effective hybrid peptides in triggering a protective immune response does not guarantee in any way, with reasonable expectation of success, which in fact it is, when transposed into an in vivo system. There are many variables present in the context of an immune response, with the orchestrated participation of several components, which are directly and indirectly influenced by many other variables. In this sense, as it is impossible to predict or control this complex range of factors beforehand, the elaboration of new synthetic peptide entities that function satisfactorily as protective vaccines represents a legitimate challenge.

The present invention demonstrates below the experimental results of immunogenicity assays with BALBc mice and ox serum of 8 (P28, P41, P42, P44, P50, P51, P51, P53 and P54) of the 14 hybrid peptides disclosed by the present invention and synthesized by the company GenOne Biotechnologies®.

The novel hybrid peptides developed by the present invention received abbreviations: P of peptide+the number corresponds to the amount of aa residues in each fragment.

TABLE 2

Hybrid Peptides

| Acronym* | Sequence | Number of residues | SEQ ID NO: |
|---|---|---|---|
| P28 | SKVASVEYILAARGGGGQVDRLANALGK | 28aa | 20 |
| P41 | SSVSSQSDQASTSSQLGGGGAMGDSVHW KVKPVDNKLFIMP | 41aa | 21 |
| P42 | LAESTEGNLEEVWILGKGGGGDELSKKV CGKGTTSGSTNQCG | 42aa | 22 |
| P44 | GASTDDAAAAAKIVAMAYGRGGGGASS VDALTATKLVAAALGH | 44aa | 23 |
| P50 | GASTDDAAAAAKIVAMAYGRGGGGTIVP VKTFDDGALTYFQFYDNNKVIP | 50aa | 24 |
| P51 | LAESTEGNLEEVWILGKGGGGFSESMKA LIKKYVDTSKPTIYVDQGTVMKV | 51aa | 25 |
| P53 | SKVASVEYILAARGGGGQVDRLANALGK GGGGAMGDSVHWKVKPVDNKLFIMP | 53aa | 26 |
| P54 | SECVSLQPTDSSSASGQQQEGGGGLQGH MIDAVLETAINSDIPGVLRAIVSRDV | 54aa | 27 |
| P48 | SSAGGQQQESSVSSGGGGLQGHMIDAVL ETAINSDIPGVLRAIVSRDV | 48aa | 28 |
| P73 | AEDDKQQQQNQSNVVQAISAVFQRGGGG GASTDDAAAAAKIVAMAYGRGGGAMGD SVHWKVKPVDNKLFIMP | 73aa | 29 |
| P55 | DAAGRVDFKVHNFDWSAPEPKGGGGLQG HMIDAVLETAINSDIPGVLRAIVSRDV | 55aa | 30 |
| P52 | NKDTGIASFNFAYFGGELGVRGGGGGTI VPVKTFDDGALTYFQFYDNNKVIP | 52aa | 31 |
| P57 | KKSNEDTASVFLLGKELAYDTARGGGGL QGHMIDAVLETAINSDIPGVLRAIVSRD V | 57aa | 32 |
| P68 | TKGEAKKWGNAIESATGTTSGGGGSECV SLQPTDSSSASGQQQEGGGGASSVDAL TATKLVAAALGH | 68aa | 33 |

*Acronym: P = peptide + number corresponding to the size of the peptide sequence (number of amino acid residues (aa)).

Immunogenicity Test

Synthetic Peptides

Lyophilized synthetic peptides were resuspended in ultrapure sterile water, as indicated concentration for each one of them, wherein the concentration ranged from 1.0 to 1.3 mg/mL.

Immunization of Mice

The immunogenicity of each peptide was checked immunizing BALB/c mice, approximately six weeks old, with 10 mg of protein (Machado et al., 1994). The mice were divided into groups of three animals each. The groups were: P28, P41, P42, P44, P50, P51, P53, P54, Pool (mice inoculated with a pool of peptides, in the case with all 8 hybrid peptides) and negative control group. For inoculations, the peptides were emulsified in Freund's complete adjuvant (Sigma) and inoculated intramuscularly in the quadriceps. Two further immunizations, on the 14th and 28th day after inoculation, were performed using incomplete Freund's adjuvant (Sigma). Each inoculation was carried out using 10 µg/mL of each peptide. Negative control mice were inoculated with sterile saline in place of the peptides and also emulsified in adjuvant. Blood samples were collected by intracardiac puncture on the 10th day after the last immunization and the sera obtained were stored at −20° C. until evaluated by Dot-ELISA and Western-blotting assays.

Immunization of Calf

The immunogenicity of the synthetic peptides was verified by immunizing a previously tested calf with negative results for *Anaplasma marginale*, *Babesia bovis* and *Babesia bigemina* by serology and PCR. For inoculations, a peptide pool (SEQ ID NO: 20, SEQ ID NO: 21, SEQ ID NO: 23, SEQ ID NO: 25 and SEQ ID NO: 26) was emulsified in Freund's complete adjuvant (Sigma) and, inoculated intramuscularly in the quadriceps. Two further immunizations, on the 14th and 28th day after inoculation, were performed using incomplete Freund's adjuvant (Sigma). Each inoculation was done using 100 µg/mL of each peptide. Blood samples were collected by jugular puncture on the 10th day after the last immunization and the sera obtained were stored at −20° C. until evaluated by Dot-ELISA and Western-blotting assays.

Immunogenicity Analysis of Peptides by Dot-ELISA

Synthetic peptides were used as antigen in the Dot-ELISA technique to verify their ability to react with specific antibodies present in the serum of BALB/c mice, as well as in calf serum, all immunized. The technique was performed as described by Machado et al. (1994), with minor modifications. Briefly, small nitrocellulose discs were cut using a paper punch and each disc arranged in a flat bottom 24-well culture plate well. 4 µg/mL of each synthetic peptide alone, as well as the peptide pool, were deposited on each disc. The discs were dried at room temperature and then blocked for 12 hours at room temperature with 300 mL TBS buffer (0.1 M Tris, 0.1 M NaCl and 0.5% Tween 20; TBS-Tween 20), plus 5% skim milk powder. Test sera were diluted 1:25 (mice and calf) in TBS-Tween 20 containing 5% skim milk powder and incubated for 120 minutes at room temperature and under constant stirring. Then the discs were subjected to two washes with TBS-Tween 20 plus 5% skim milk powder and one wash with TBS-Tween 20 (5 min interval between each wash). To each mouse serum disc was added the alkaline phosphate-coupled anti-mouse conjugate (anti-mouse IgG goat IgG, Sigma A-3562) diluted 1:30,000 in TBS-Tween 20 plus 5% of skim milk powder. To calf serum-containing discs, it was added alkaline phosphate-coupled anti-bovine conjugate (anti-cattle IgG rabbit IgG, Sigma A-0705) diluted 1:30,000 in TBS-Tween 20, plus 5% skim milk powder. After one hour incubation with the appropriate conjugates, washes were followed as in the previous step. The reaction was revealed by adding the enzyme substrate 5-bromo-4-chloro-3-indolyl phosphate and nitroethanolic blue chloride using the Alkaline Phosphatase Conjugate Substrate kit (Bio-Rad) according to the manufacturer's specifications.

Reactivity of Synthetic Peptides by Western Blotting

Samples of synthetic peptides were analyzed by Western blotting. To this end, initially, the samples were submitted to polyacrylamide gel electrophoresis under denaturing conditions, according to the technique recommended by Laemmli (1970). Based on the sample volume 2× concentrated sample buffer (250 mM Tris-HCl pH 6.8, 40% glycerol, 8% SDS, 20% β-mercaptoethanol and 0.008% bromophenol blue) was added. The samples were homogenized, incubated for 5 minutes at 100° C. and applied to the gel. The separation gel was prepared at a concentration of 12% polyacrylamide in buffer (1.875 M Tris, pH 8.8 and 1% SDS) and 5% polyacrylamide for buffer packaging gel (1.875 M Tris, pH 6.8 and 0.5% SDS). Electrophoresis was performed in Tris-Glycine Running Buffer (50 mM Tris, pH 8.6, 1.92 M Glycine and 1% SDS) at 100 V for up to 3 hours and 30 minutes at 0° C. in the Mini-Protean II system (Bio-Rad).

Synthetic peptides processed on the polyacrylamide gel (SDS-PAGE) were transferred to the nitrocellulose membrane for analysis by Wester blot (TOWBIN et al., 1979). The nitrocellulose membrane (Merck) was previously incubated in ice cold transfer buffer (0.58% Tris Base pH 8.3, 20% methanol and 0.29% glycine). For this, the membrane was placed in the "Mini Trans-Blot" (Bio-Rad) electrotransfer system containing the same buffer and the transfer was performed at 100 V for 90 minutes. The membrane was incubated in TBS-Tween (10 mM Tris-HCl pH 7.5; 150 mM NaCl, 0.05% Tween-20) plus 5% skim milk powder for 12 hours at 4° C. under low agitation, for saturation of nonspecific binding sites. The membrane was then incubated with each serum from each mouse alone or incubated with calf serum for 2 hours at room temperature under slow stirring. It was then subjected to three consecutive 10-minute washes with the same solution under slow agitation.

For detection of antigen-antibody complex, the membrane was incubated with alkaline phosphatase coupled anti-mouse conjugated (goat IgG anti-mouse IgG, Sigma A-3562) diluted 1:30,000 in TBS-Tween, or alkaline phosphatase coupled anti-cattle conjugated (rabbit IgG anti-bovine IgG, Sigma A-0705), diluted 1:30,000 in TBS-Tween. The membrane was subjected to three washes as described above and the development occurred by addition of the BCIP-NBT enzyme substrate using the Alkaline Phosphatase Conjugate Substrate Kit (Bio-Rad, Cat #170-6432). according to the manufacturer's instructions.

Indirect Immunofluorescence Reaction (IFA)

The prepared *A. marginale* antigen-containing blood smear slides were removed from the freezer and thawed at room temperature. In each antigen-containing circle, 10 mL of each test serum was added, which diluted at a concentration of 1:25 (for mice) and 1:80 (for cattle). The slides were then incubated in a humid chamber at 37° C. for 30 minutes and then subjected to three washes in PBS by immersion for five minutes each. After drying at room temperature, the slide circles were covered with 10 mL of the fluorescein isothiocyanate (Sigma) conjugated mouse/ bovine anti-IgG antibody, diluted 1:64 for mice and 1:300 for cattle, in PBS solution containing 1 mg % Evans Blue. The slides were again incubated and washed as described above. After drying the slides, they were coverslipped using a buffered glycerine at a 9:1 ratio of glycerine/0.5 M carbonate-bicarbonate buffer pH 9.6 and then observed under a fluorescence microscope (Olympus, BX-FLA).

Dot-ELISA Analysis

Sera from mice and calves immunized with hybrid synthetic, alone or in pool peptides, as appropriate, demonstrated reactivity in accordance with the results listed in Tables 3 and 4.

In particular, it was observed that calf serum inoculated with the peptide pool reacted with peptides P41, P44, P51 and P53, as well as with the peptide pool. A bovine known as serologically positive for *A. marginale* reacted with the peptide pool, as well as the serum from a bovine known as serologically negative for *A. marginale* did not react in the test.

Furthermore, it was observed that sera from mice inoculated with hybrid peptides alone reacted with peptides P42, P44, P51 and P54. Mouse sera inoculated with the peptide pool also reacted with P28, P51, P53 and P54. Mice sera of the negative control group showed no reactivity in the test.

TABLE 3

Dot-ELISA Result for Reactivity of Each Synthetic Hybrid Peptide with Serum from Immunized Animals

| Peptide Reactivity | Mice serum inoculated with isolated peptides | | | Mice serum inoculated with pool | Mice serum inoculated with Saline (Negative Control) | Calf serum inoculated with pool |
|---|---|---|---|---|---|---|
| | 1 | 2 | 3 | | | |
| P28 | — | — | — | — | — | — |
| P41 | — | — | — | — | — | X |
| P42 | X | — | — | — | — | — |
| P44 | X | X | X | — | — | X |
| P50 | — | — | — | — | — | — |
| P51 | — | X | X | X | — | X |
| P53 | — | — | — | X | — | X |
| P54 | X | X | X | X | — | — |

— = Did not react;
X = Reacted

TABLE 4

Dot-ELISA Result for Synthetic Hybrid Peptide Pool Reactivity with Serum from Immunized Animals

| Animal serum | | Inoculated with | Reaction with pool of peptides |
|---|---|---|---|
| Mouse | 1 | P28 | — |
| | 2 | | X |
| | 3 | | — |
| | 1 | P41 | — |
| | 2 | | — |
| | 3 | | — |
| | 1 | P42 | — |
| | 2 | | — |
| | 3 | | — |
| | 1 | P44 | — |
| | 2 | | — |
| | 3 | | — |
| | 1 | P50 | — |
| | 2 | | — |
| | 3 | | — |

TABLE 4-continued

Dot-ELISA Result for Synthetic Hybrid Peptide Pool Reactivity with Serum from Immunized Animals

| Animal serum | | Inoculated with | Reaction with pool of peptides |
|---|---|---|---|
| | 1 | P51 | — |
| | 2 | | X |
| | 3 | | — |
| | 1 | P53 | X |
| | 2 | | X |
| | 3 | | X |
| | 1 | P54 | — |
| | 2 | | X |
| | 3 | | — |
| | 1 | Salina (negative control) | — |
| | 2 | | — |
| | 3 | | — |
| Calf | | Pool | X |
| Bovine positive for *A. marginale* | | | X |
| Bovine negative for *A. marginale* | | | — |

— = Did not react;
X = Reacted

Also, sera from serologically positive cattle for *A. marginale* reacted with synthetic peptides P28, P44, P53 and P54. Sera from vaccinated cattle for *A. marginale* also reacted with synthetic peptides P28 and P44. The serologically negative bovine serum for *A. marginale* did not react with any synthetic peptide.

Western Blotting Analysis

Synthetic peptides that obtained reactivity, either with mouse serum or calf serum inoculated with the peptide pool, by the Dot-ELISA test, were also analyzed by Western blotting. The Western-blotting corroborated the data obtained with the Dot-ELISA, wherein the calf serum showed reactivity to peptides P41, P44, P51 and P53. Calf serum even reacted with the peptide pool. The positive serologically bovine serum for *A. marginale* (positive control) also reacted with the pool of peptides in the test, while the serologically negative bovine serum for *A. marginale* (negative control) resulted no reaction. Bands below 10 kDa were detected, corresponding to synthetic peptides.

They reacted in the serum test of mice inoculated with synthetic peptides P42, P44, P53 and P54.

Indirect Immunofluorescence Reaction (IFR) Analysis

The calf inoculated with peptide pool was positive for *A. marginale*. Also positive for *A. marginale* were mice inoculated with synthetic peptides P42, P50 and animals inoculated with a peptide pool.

Field Vaccine Efficiency Test

Immunization of Cattle with Pool of Hybrid Synthetic Peptides

Animal Selection

It was selected 23 cattle for carrying out field experiments. All selected animals were found to be negative for *A. marginale* by the Indirect Immunofluorescence Reaction (IFR) and by the indirect enzyme immunoassay (ELISA-test), according to protocols previously described. The animals were divided into two groups according to the parameter to be analyzed, wherein the vaccinated group consisting of 18 animals of the Dutch breed, 16-20 months age, received immunization with synthetic hybrid peptides, and the non-vaccinated group, where applicable, consisting of five animals that did not receive immunization with synthetic hybrid peptides. It is important to highlight that on the farm where the vaccine was tested, anaplasmosis was a prevalent disease, leading to considerable expense in handling animal treatment.

Vaccine Preparation

The vaccine consisted of a pool of synthetic hybrid peptides (SEQ ID NO: 20, SEQ ID NO: 21, SEQ ID NO: 23, SEQ ID NO: 25 and SEQ ID NO: 26). In all immunizations, the immunogen consisted of 100 μg of each peptide from the synthetic peptide pool reported above (totaling 500 μg of synthetic peptides per animal). Lyophilized synthetic peptides were resuspended in about 1.0 mL) of sterile ultrapure water, concentration as indicated for each one, varying from 1.0 to 1.3 mg/mL.

Cattle Immunization

Each animal in the vaccinated group received 3 doses of the vaccine, 15 days apart. The first dose consisted of the synthetic peptides emulsified with complete Freund's adjuvant (Sigma). The second and third doses consisted of the synthetic peptide emulsified with incomplete Freund's adjuvant (Sigma). All inoculations occurred intramuscularly in the neck board region. Fifteen days after the third dose of vaccine, the animals were challenged with *A. marginale* parasitized calf blood, being 500 μL/animal, that is, $1.02 \times 10^5$ parasites/mL, subcutaneously.

Collection of Samples and Evaluated Parameters

Blood samples from each animal were collected by puncture of the jugular vein according to the following design: before the first dose (sampling 1), on the day and immediately before the third dose (sampling 2) and 15 days after the third dose (sampling 3). Thirty-two days after the third dose, the animals were challenged and the following samples were also performed: 35 days after challenge (collecting 4) and 45 days after challenge (collecting 5).

Animal blood samples were collected in appropriate tubes containing EDTA anticoagulant, and the following analyzes for characterization of animal health and immune response were performed, according to the protocols described herein and/or known by a person skilled in the art: hematological evaluation, immunophenotyping of T $CD4^+$ and T $CD8^+$ lymphocytes, evaluation of cytokine messenger RNA expression by blood cells and evaluation of parasitic load in the blood of animals. In addition, sera obtained from EDTA-free blood were used to detect anti-*Anaplasma marginale* antibodies by ELISA and Dot-ELISA tests. In addition, temperature and body weight data were collected from each animal. Finally, throughout the period, a behavioral and mucosal staining evaluation was also performed to add to the other observations and to enable the conclusion regarding the health of experimental (sick or non-sick) cattle.

Animals that during the course of the experiment showed behavioral changes (bovine sadness and lack of appetite) and conjunctival and vaginal or preputial mucosal staining (turning yellowish-white) were considered as having clinical symptoms of the disease and could be treated after laboratory tests.

Animal Challenge

For verifying vaccine efficacy and protection of animals immunized with synthetic hybrid peptides, the animals were challenged with *A. marginale* strain thirty-two days after the 3$^{rd}$ vaccine dose.

To this end, a sample of the *A. marginale* strain (Jaboticabal strain) maintained in liquid nitrogen was thawed and inoculated in intact calf and with negative molecular and serological tests for *Anaplasma marginale, Babesia bovis* and *Babesia bigemina*. The parasitemic load of *Anaplasma marginale* reached its highest value of $1,385 \times 10^5$ DNA copies, 23 days after infection. From this animal, 50 mL of blood were collected for the preparation of challenge inoculum. It was performed counting of the parasites in smears stained by Giemsa stain in squared areas of 100 lens, counting 1000 the number of parasitized red blood cells, establishing thereby parasitemia of $1.02 \times 10^8$ parasites. The animals were inoculated with calf blood parasitized with *A. marginale*, being 500 μL/animal, that is, $1.02 \times 10^5$ parasites/mL subcutaneously.

Hematological Evaluation

For hematological evaluation of the animals before vaccination and after challenge (samplings 4 and 5), complete blood count was performed in a commercial laboratory. Of particular relevance, it was analyzed the percentage of hematocrit, indicating the reduction in the number of red blood cells (anemia). It was considered for cattle, as a change in the percentage of hematocrit, values below 24%.

T $CD4^+$ and T $CD8^+$ Lymphocyte Immunophenotyping in Cattle Blood Cells by Flow Cytometry Flow cytometry analysis of the T cell population ($CD4^+$ and $CD8^+$ T cell percentage and Median Fluorescence Intensity (MFI) of each marker ($CD4^+$ and $CD8^+$) on the cell surface), indicative of the immune response produced, was performed according to the methodology of Lollo et al. (2016) from peripheral blood (samplings 1, 2, 3 and 5).

Briefly, 100 μl of whole blood with EDTA were transferred to 1.5 mL conical microtubes and 2 μl of each antibody (anti-CD4 MCA1653F—Bio-Rad and anti-CD8-MCA837PE—Bio-Rad) was added. The blood containing the antibodies was incubated for 30 minutes at 4° C. in the dark. Then, it was added 1.8 mL of lysis buffer (Tris-ammonium chloride 0.83% sterile) preheated to 37° C. and incubated for 10 minutes at 37° C. The material was then centrifuged at 1,800 rpm for 10 minutes at room temperature and the supernatant discarded. The samples were washed twice with 1 mL of sterile PBS, centrifuging under the same conditions to remove unbound antibodies. The final cell button was resuspended in 200 μL of 1% PBS-Formaldehyde and transferred to cystometry-specific polystyrene test tubes (BD Pharmingen, Cat. No. 352008) and kept in a refrigerator covered with aluminum foil. Cell preparations were analyzed on the FACScanto flow cytometer (Becton, Dickison and Company; San Jose, Calif., USA) (20,000 events per sample). The selection of cell subpopulations found in the different samples analyzed was made possible through pre-established acquisition protocols (Byrne et. al., 2000).

EVALUATION of mRNA Expression of Cytokines by Blood Cells

For characterizing the type of response produced by the immune system cells of cattle vaccinated in samplings 3 and 4, the expression of messenger RNA (mRNA) of cytokines IL-2, TNF-α, IFN-γ, IL-12 and IL-10 from cells in the peripheral blood. Samples related to sampling 1 were used as calibrators.

Total RNA Extraction

Blood samples were placed in 2.0 mL conical microtubes containing 1.2 mL of RNALater—RNA Stabilization Reagent (Ambion, Life Technologies of Brazil) for each 500 µL of blood in each sample. Total blood RNA extraction was performed with RiboPure—Blood (Ambion, Life Technologies of Brazil), following the manufacturers guidelines. Total RNA obtained from all samples was measured on the Nanodrop ND1000 spectrophotometer (Thermo Scientific, USA) at 260 and 280 nm. They were also analyzed with the aid of Bioanalyserequipment. These samples were stored at −20° C. until mRNA reverse transcription was performed.

RT-PCR (Reverse Transcription-Polymerase Chain Reaction)

Reverse transcription was performed using the GoScript Transcription System (Promega, USA) to obtain complementary DNA (cDNA) from mRNA using the same amount of 1 µg total RNA for all samples and according to the manufacturers reaction conditions. The cDNA was used as a template in the Quantitative Real Time PCR (qPCR) technique to determine the expression profile of the cytokines of interest. The cDNA was stored at −20° C. until the moment of use.

Quantitative Real Time PCR

The qPCT was performed in a final volume of 20 µl for the following cytokines and endogenous gene: IL-2, IL-10, IL-12, IFN-γ and H3F3A containing 10 µL of Master Mix (SYBR Green JumStart Taq ReadMix, SIGMA), 2 µL of PrimeTime Assay 10× concentrate, specific for each cytokine (PrimeTime Std qPCR Assay, IDT, USA), 5 µL of DNAse and RNAse free water and 1 µL of cDNA. The qPCR reaction was performed in a final volume of 25 µl for the cytokine TNF-α, containing 12.5 µL of Master Mix (SYBRGreen JumStart Taq ReadMix, SIGMA), 0.75 µL of concentrate PrimeTime Assay 10×, specific for each cytokine (PrimeTime Std qPCR Assay, IDT, USA), 9.5 µL DNAse and RNAse free water and 1.5 µL cDNA. The reaction took place in a CFX-96 (Bio-Rad) apparatus using 96-well plates (Low 96-well Clear, Bio-Rad) and adhesives (Microseal '13' Film, Bio-Rad). For each cytokine and endogenous gene, specific PrimeTime Assay was acquired, as per Table 5 (Puech et al., 2015; Konnai et al., 2003). The reaction conditions for the TNF-α cytokine and endogenous gene H3F3A were 95° C. for 10 minutes, followed by 44 cycles of 95° C. for 30 seconds, 60° C. for 30 seconds and 72° C. for 45 seconds. Reaction conditions for cytokine IL-2 was 94° C. for 2 minutes, followed by 44 cycles of 94° C. for 15 seconds, 53° C. for 30 seconds and 72° C. for 45 seconds. Reaction conditions for cytokine IL-10 were 94° C. for 2 minutes, followed by 44 cycles of 94° C. for 15 seconds, 56° C. for 30 seconds and 72° C. for 45 seconds. Reaction conditions for IL-12 cytokine were 94° C. for 2 minutes, followed by 44 cycles of 94° C. for 15 seconds, 55° C. for 30 seconds and 72° C. for 45 seconds. The reaction conditions for IFN-γ cytokine were 94° C. for 2 minutes, followed by 44 cycles of 94° C. for 15 seconds, 55° C. for 30 seconds and 72° C. for 45 seconds. For each reaction, the samples were processed in duplicate. Negative controls consisted of autoclaved ultra pure water instead of cDNA, and the positive control consisted of the standard curves used in each reaction. The amplification result was used to normalize the reaction and it was used as calibrator, samples collected from calves of sampling 1. The relative quantification was performed using equation $2^{-\Delta\Delta C_T}$, wherein $\Delta Ct = Ct$ (target)−Ct (reference gene control) and $\Delta\Delta Ct = \Delta Ct$ (sample)−$\Delta Ct$ (calibrator) (Livak and Schmittgen, 2001).

TABLE 5

Oligonucleotides Primers

| Target | Sequence | | SEQ ID NO: |
|---|---|---|---|
| IL-2 | 5'-TTTTACGTGCCCAAGGTTAA-3' | (F) | 34 |
|  | 5'-CGTTTACTGTTGCATCATCA-3' | (R) | 35 |
| IFN-γ | 5'-ATAACCAGGTCATTCAAAGG-3' | (F) | 36 |
|  | 5'-ATTCTGACTTCTCTTCCGCT-3' | (R) | 37 |
| TNF-α | 5'-CCAGAGGGAAGAGCAGTCC-3' | (F) | 38 |
|  | 5'-GGCTACAACGTGGGCTACC-3' | (R) | 39 |
| IL-12 | 5'-AACCTGCAACTGAGACCATT-3' | (F) | 40 |
|  | 5'-ATCCTTGTGGCATGTGACTT-3' | (R) | 41 |
| IL-10 | 5'-TGCTGGATGACTTTAAGGG-3' | (F) | 42 |
|  | 5'-AGGGCAGAAAGCGATGACA-3' | (R) | 43 |
| H3F3A | 5'-GAGGTCTCTATACCATGGCTC-3' | (F) | 44 |
|  | 5'-GTACCAGGCCTGTAACGATG-3' | (R) | 45 |

Cattle Parasitic Load Assessment

DNA Extraction from Cattle Blood for Infection Detection

To verify the parasitic load of *Anaplasma marginale* in the cattle blood samples (samplings 1 to 5), DNA extraction was performed using the commercial DNeasy Blood & Tissue Kit (Qiagen) according to the manufacturer's instructions. As positive reaction control, samples of *Anaplasma marginale* kept in culture were used. After extraction and concentration dosage, the DNA was stored at −20° C. for q PCR.

Amplification of DNA Fragments by Real-Time Quantitative PCR for msp1b Gene of *A. marginale*

The qPCR was performed by the method described by Carelli et al. (2007), with modifications to the msp1β gene. The reaction was carried out with a final mix volume of 10 µL containing 1 µL of genomic DNA, 5.0 µL of GoTaq Probe qPCR Master Mix (Promega), 0.9 µM of each oligonucleotide primer (direct: 5'-TTGGCAAGGCAGCAGCTT-3' (SEQ ID NO: 46) and inverse: 5'-TTCCGCGAGCATGTG-CAT-3' (SEQ ID NO: 47)) and 0.2 µM hydrolysis probe (6FAM-5'-TCGGTCTAACATCTCCAGGCTTTCAT-3'-BHQ1 (SEQ ID NO: 48)). The cycles were performed under the following conditions: 2 minutes at 50° C., 10 minutes at 95° C. and 40 cycles of 15 seconds at 95° C. and 1 minute at 60° C. Amplification reactions were conducted in a CFX96 Thermal Cycler (BioRad, Hercules, Calif., United States) thermal cycler apparatus. All samples were tested in duplicates. Target DNA copy number quantification/µL was performed using the pSMART plasmid (Integrated DNA Technologies, Coralville, Iowa, USA) containing the 95 bp target sequence for *A. marginale* DNA amplification (msp1β gene). Reaction efficiency was calculated by a standard curve obtained from serial dilutions of plasmid DNA containing the target sequence. Serial dilutions were made to construct a standard curve with different concentrations of plasmid DNA containing the target sequence ($2.0 \times 10^7$ copies/µL to $2.0 \times 10^0$ copies/µL). The number of copies of plasmids was determined according to the formula (Xg/µL DNA/[plasmid size (bp)$\times 660$])$\times 6.022 \times 10^{23} \times$copies of plasmid/µL. Sterile ultrapure water (Qiagen, Madison, USA) was used as negative reaction control.

Immunogenicity Evaluation of Peptides by ELISA-Test and Dot-ELISA

Synthetic peptides were used as the antigen Dot-ELISA technique, and the sera were used to detect antibodies by ELISA-test, in order to verify their reaction capability with specific antibodies in bovine (immunized and unimmunized) serum (samplings 1, 2 and 3). The techniques were performed as previously described herein.

Body Temperature Assessment

The animals temperature of the vaccinated group was evaluated within 3 days prior to challenge of the pre-infection animals. The temperature of the animals of both groups was also evaluated every 1 or 2 days after infection (total of 41 times evaluated). The assessment was performed by inserting the thermometer in the anal area, according to procedure known by a person skilled in the art. The temperature was considered altered when above 39.5° C.

Weight Assessment

The weight of the animals in the vaccinated group was evaluated before vaccination, on the day of the challenge and after the challenge (sampling 5) by the use of a metric strip on the most circumferential abdominal region, according to a technique known by a person skilled in the art.

Field Vaccine Efficiency Test Results

Hematocrit Analysis

Fourteen animals from the vaccinated group had hematocrit values below 30%, but were able to recover at the end of the observation, indicating that they had passed the challenge and were able to resist the multiplication of the agent. No animals in the vaccinated group had values below 24% and were not considered anemic.

T Cell Population Analysis

Analysis of the $CD4^+$ and $CD8^+$ T-cell population in vaccinated cattle indicated a slight increase in the percentage of $CD4^+$ and $CD8^+$ T-cell populations from samplings 2, 3 and 5 compared to sampling 1, in which the increase in $CD4^+$ T cells was slightly higher than $CD8^+$ T cells. As to the MFI analysis, indicated increase of these markers on the surface of the cells. Overall, these data reveal the cellular activation and responsiveness of animals to stimuli (vaccination and challenge).

Analysis of the Cytokines Produced

Analysis of cytokines produced in response to immunization (sampling 3) and challenge (sampling 4) in relation to sampling 1 indicated increased expression of IFN-γ and IL-12 from sampling 3 to 4, indicating possible increased expression or IFN-γ producing CD4 lymphocyte population. This result indicates the importance of cellular immune response.

Parasite Load

Except for the samples used as negative control, all bovine blood samples were considered positive in view of the constant field challenge at the times evaluated. However, the values were considered the low (average of about $0.5$-$1 \times 10^5$ infected erythrocytes per mL of blood in the samples 1, 3 and 5), and sufficient to maintain stimulation without clinical symptoms in the vaccinated animals.

Evaluation of Peptide Immunogenicity by Dot-ELISA and ELISA-Test

Only 2 animals from the vaccinated group did not respond to any peptide. The others showed response to vaccine peptides (3 to 5 peptides) by Dot-ELISA, indicating that it was possible to trigger immune response against synthetic peptides. However, even those who do not presented response in the test performed did not get sick.

Also, all animals (with antibody detection by ELISA test) (except 4 animals from the vaccinated group) were serologically negative after the third peptide vaccination, but after challenge, became positive (except two animals). The presence of antibodies indicates that the animal has come into contact with the parasite and may or may not induce protection. Still, the non-responsiveness of some animals does not mean that they would not be protected.

Temperature

From the vaccinated group, 5 animals showed one to two temperature peaks during the evaluation time. However, only 2 of these presented the other expected symptoms of the disease (alteration of mucosal color and behavior), requiring treatment. The remaining 3 animals were not treated because the temperature was naturally normalized and did not show the other expected symptoms of the disease. In the control group, 3 animals presented temperature changes, and 2 required treatment.

Animal Weight

All animals increased in weight within 42 days after experimental infection, even if challenged by the agent. On average, each animal gained about 25.6 kg, indicating that they underwent infection without presenting the characteristic weight loss as observed in the sick animals.

Conclusion

Taken together, the results from the analysis indicated that 88.9% of vaccinated animals were able to control the infection (16/18 vaccinated and challenged cattle), not requiring treatment (either by the absence of characteristic disease symptoms, as observed, or by the natural normalization of the parameters during the evaluation). All animals (including those treated) remain protected even after 5 months of vaccination, leading to financial savings. In the same period, non-vaccinated animals became ill and required recurrent treatment.

Such efficiency, added to the synthetic production advantage of the hybrid peptides according to the present invention, represents an important advance over the other vaccines already tested against anaplasmosis.

BIBLIOGRAPHIC REFERENCES

Abbott, J. R., Palmer, G. H., Kegerreis, K. A., Hetrick, P. F., Howard, C. J., Hope, J. C., Brown, W. C. Rapid and long-term disappearance of CD4+ T lymphocyte responses specific for *Anaplasma marginale* major surface protein-2 (MSP2) in MSP2 vaccinates following challenge with live *A. marginale*. Journal of Immunology, v. 174, n. 11, p. 6702-6715, 2005.

Abbott, J. R., Palmer, G. H., Howard, C. J., Hope, J. C., Brown, W. C. *Anaplasma marginale* major surface protein 2 CD4+-T-cell epitopes are evenly distributed in conserved and hypervariable regions (HVR), whereas linear B-cell epitopes are predominantly located in the HVR. Infection and Immunity, v. 75, n. 12, p. 7360-7366, 2004.

Agnes, J. T., Brayton, K. A., LaFollett, M., Norimine, J., Brown, W. C., Palmer, G. H. Identification of *Anaplasma marginale* Outer Membrane Protein Antigens Conserved between *A. marginale* Sensu Stricto Strains and the Live *A. marginale* subsp. *centrale* Vaccine. Infection and Immunity, v. 79, n. 3, p. 1311-1318, 2011.

Araújo, F. R., Costa, C. M., Ramos, C. A. M., Farias, T. A., Souza, I. E. F., Melo, E. S. P., Elisei, C., Rosinha, G. M. S., Soares, C. O., Fragoso, S. P., Fonseca, A. H. IgG and IgG2 antibodies from cattle naturally infected with *Anaplasma marginale* recognize the recombinant vaccine candidate antigens VirB9, VirB10, and elongation factor-Tu. Mem. Inst. Oswaldo Cruz, v. 103, n. 2, p. 186-190, 2008.

Brown, W. C., Brayton, K. A., Styer, C. M., Palmer, G. H. The Hypervariable Region of *Anaplasma marginale* Major Surface Protein 2 (MSP2) Contains Multiple Immunodominant CD4+ T Lymphocyte Epitopes That Elicit Variant-Specific Proliferative and IFN-Responses in MSP2 Vaccinates. J Immunol, v. 170, p. 3790-3798, 2003.

Brown, W. C., Palmer, G. H., Brayton, K. A., Meeus, P. F. M., Barbet, A. F., Kegerreis, K. A., McGuire, T. C. CD4+T Lymphocytes from *Anaplasma marginale* Major Surface Protein 2 (MSP2) Vaccinees Recognize Naturally Processed Epitopes Conserved in MSP3. Infection and Immunity, v. 72, n. 6, p. 3688-3692, 2004.

Crosby, F. L., Brayton, K. A., Magunda, F., Munderloh, U. G., Kelley, K. L., Barbet, A. F. Reduced Infectivity for Cattle of an Outer Membrane Protein mutant of *Anaplasma marginale*. Applied and Environmental Microbiology, v. 81, n. 6, p. 2206-2214, 2015.

Garcia-Garcia, J. C., La Fuente, J., Kocan, K. M., Blouin, E. F., Halbur, T., Onet, V. C., Saliki, J. T. Mapping of B-cell epitopes in the N-terminal repeated peptides of *Anaplasma marginale* major surface protein 1a and characterization of the humoral immune response of cattle immunized with recombinant and whole organism antigens. Veterinary Immunology and Immunopathology, v. 98, p. 137-151, 2004.

Gentilucci, L., De Marco, R., Cerisoli, L. Chemical Modifications Designed to Improve Peptide Stability: Incorporation of Non-Natural Amino Acids, Pseudo-Peptide Bonds, and Cyclization. Current Pharmaceutical Design, v. 16, p. 3185-3203, 2010.

Hammac, G. K., Ku, P. S., Galletti, M. F., Noh, S. M., Scoles, G. A., Palmer, G. H., Brayton, K. A. Protective immunity induced by immunization with a live, cultured *Anaplasma marginale* strain. Vaccine, v. 31, n. 35, p. 3617-3622, 2013.

Junior, D. S. G., Araújo, F. R., Junior, N. F. A., Adi, S. S., Cheung, L. M., Fragoso, S. P., Ramos, C. A. N., Oliveira, R. H. M., Santos, C. S., Bacanelli, G., Soares, C. O., Rosinha, G. M. S., Fonseca, A. H. Analysis of membrane protein genes in a Brazilian isolate of *Anaplasma marginale*. Memórias do Instituto Oswaldo Cruz, v. 105, n. 7, p. 843-849, 2010.

Kim, Y., Sette, A., Peters, B. Applications for T-cell epitope queries and tools in the Immune Epitope Database and Analysis Resource. J. Immunol. Methods, v. 374, p. 62-69, 2011.

Lasmar, P. V. F., de Carvalho, A. U., Filho, E. J. F., Bastos, C. V., Ribeiro, M. F. B. Evaluating the effectiveness of an inactivated vaccine from *Anaplasma marginale* derived from tick cell culture. Rev. Bras. Parasitol. Vet., Jaboticabal, v. 21, n. 2, p. 112-117, 2012.

Lopez, J. E., Guy, H. P., Brayton, K. A., Dark, M. J., Leach, S. E., Brown, W. C. Immunogenicity of *Anaplasma marginale* Type IV Secretion System Proteins in a Protective Outer Membrane Vaccine. Infection and Immunity, v. 75, n. 5, p. 2333-2342, 2007.

Machado, R. Z., Montassier, H. J., Pinto, A. A., Lemos, E. G., Machado, M. R., Valadao, I. F., Barci, L. G., Malheiros, E. B. An enzyme-linked immunosorbent assay (ELISA) for the detection of antibodies against *Babesia bovis* in cattle. Veterinary Parasitology, v. 71, p. 17-26, 1997.

McGuire, T. C., Stephens, E. B., Palmer, G. H., McElwain, T. F., Lichtensteiger, C. A., Leib, S. R., Barber, A. F. Recombinant vaccinia virus expression of *Anaplasma marginale* surface protein MSP-1a: effect of promoters, leader sequences and GPI anchor sequence on antibody response. Vaccine, v. 12, n. 5, p. 465-471, 1994.

Morse, K., Norimine, J., Hope, J. C., Brown, W. C. Breadth of the CD4+ T-cell response to *Anaplasma marginale* VirB9-1, VirB9-2, and VirB10 and MHC class II DR and DQ restriction elements. Immunogenetics, v. 64, n. 7, p. 507-523, 2012a.

Morse, K., Norimine, J., Palmer, G. H., Sutten, E. L., Baszler, T. V., Brown, W. C. Association and Evidence for Linked Recognition of Type IV Secretion System Proteins VirB9-1, VirB9-2, and VirB10 in *Anaplasma marginale*. Infection and Immunity, v. 80, n. 1, p. 215-227, 2012b.

Noh, S. M., Zhuang, Y., Futse, J. E., Brown, W. C., Brayton, K. A., Palmer, G. H. The immunization-induced antibody response to the *Anaplasma marginale* major surface protein 2 and its association with protective immunity. Vaccine, v. 28, n. 21, p. 3741-3747, 2010.

Noh, S. M., Brayton, K. A., Brown, W. C., Norimine, J., Munske, G. R., Devitt, C. M., Palmer, G. H. Composition of the Surface Proteome of *Anaplasma marginale* and Its Role in Protective Immunity Induced by Outer Membrane Immunization. Infection and immunity, v. 76, n. 5, p. 2219-2226, 2008.

Santos, P. S., Sena, A. A., Nascimento, R., Araiijo, T. G., Mendes, M. M., Martins, J. R., Mineo, T. W., Mineo, J. R., Goulart, L. R. Epitope-Based Vaccines with the Anaplasma marginale MSP1a Functional Motif Induce a Balanced Humoral and Cellular Immune Response in Mice. PLoS ONE, v. 8, n. 4, e60311, 2013.

Silvestre, B. T., Rabelo, E. M., Versiani, A. F., da Fonseca, F. G., Silveira, J. A., Bueno, L. L., Fujiwara, R. T., Ribeiro, M. F. Evaluation of humoral and cellular immune response of BALB/c mice immunized with a recombinant fragment of MSP1a from Anaplasma marginale using carbon nanotubes as a carrier molecule. Vaccine, v. 32, n. 19, p. 2160-2166, 2014.

Vita, R., Overton, J. A., Greenbaum, J. A., Ponomarenko, J., Clark, J. D., Cantrell, J. R., Wheeler, D. K., Gabbard, J. L., Hix, D., Sette, A., Peters, B. The immune epitope database (IEDB) 3.0. Nucleic Acids Res, v. 43, p. D405-412, 2015.

University of Oklahoma State. Elihu, B. W., Olin, K. I., Clifton, P. C. Method of manufacturing anaplasmosis vaccine. U.S. Pat. No. 3,511,908 A. Jun. 23, 1965; May 12, 1970.

Pipano, E., Krigel, Y., Frank, M., Markovics, A., Mayer, E. Frozen Anaplasma centrale vaccine against anaplasmosis in cattle. Brazilian Journal of Veterinary Research and Animal Science, v. 142, n. 6, p. 553-556, 1986.

Diamond Laboratories, Inc. Des Moines, Iowa. Welter, C. J., Urbana, M. R. Anaplasmosis Vaccine. US841597, Jul. 14, 1969.

Louisiana State University. Hart, L. T., Luther, D. G., Todd, W. J. Anaplasma marginale antigen, antigen compositions, vaccine and process for the production of said antigen, antigen compositions and vaccine. U.S. Pat. No. 4,956,278 A, Feb. 23, 1988, Sep. 11, 1990.

The Board Of Regents For Oklahoma State University. La Fuente, J. J., Kocan, K. M., Garcia-Garcia, J. C., Blouin, E. F. Recombinant antigen MSP1a from Anaplasma marginale to reduce infections in ticks, vaccine compositions and methods of use. U.S. Pat. No. 6,979,451 B1, Oct. 30, 2000, Dec. 27, 2005.

Livak, K. J., Schmittgen, T. D. Analysis of relative gene expression data using real-time quantitative PCR and the $2^{-\Delta\Delta C_T}$ method. Methods, v. 25, p. 402-408, 2001.

Andrade, G. M., Machado, R. Z., Vidotto, M. C., Vidotto, O. Immunization of cattle using a DNA vaccine (pcDNA3.1/MSP1b) prepared from the Jaboticabal strain of Anaplasma marginale. Annals of New York Academy of Sciences, New York, v. 1026, p. 257-266, 2004.

Carelli, G., Decaro, N., Lorusso, A., Elia, G., Lorusso, E., Mari, V., Ceci, L., Buonavoglia, C. Detection and quantification of Anaplasma marginale DNA in blood samples of cattle by real-time PCR. Veterinary Microbiology, v. 124, p. 07-14, 2007.

Hartree, E. F. Determination of protein: a modification of the Lowry method that gives a linear photometric response. Analytical Biochemistry, v. 48, p. 422-427, 1972.

Puech, C., Dedieu, L., Chantal, I., Rodrigues, V. Design and evaluation of a unique SYBR Green real-time RT-PCR assay for quantification of five major cytokines in cattle, sheep and goats. BMC Veterinary Research, 11:65, 2015.

de Lollo C., de Moraes Vasconcelos D., da Silva Oliveira L. M., de Oliveira Titz T., Carneiro-Sampaio M., Jacob C. M., da Silva Duarte A. J., Sato, M. N. Impaired CD8(+) T cell responses upon Toll-like receptor activation in common variable immunodeficiency. Journal of Translational Medicine, 14(1):138, 2016.

Machado, R. Z., Valadão, C. A., Melo, W. R., Alessi, A. C. Isolation of Babesia bigemina and Babesia bovis merozoites by ammonium chloride lysis of infected erythrocytes. Brazilian Journal of Medical and Biological Research, v. 27, p. 2591-2598, 1994.

Konnai, S., Usui, T., Ohashi. K., Onuma, M. The rapid quantitative analysis of bovine cytokine genes by real-time RT-PCR. Veterinary Microbiology, v. 94, p. 283-294, 2003.

Barbosa da Silva, J., Vinhote, W. M., Oliveira, C. M., André, M. R., Machado, R. Z., da Fonseca, A. H., Barbosa, J. D. Molecular and serological prevalence of Anaplasma marginale in water buffaloes in northern Brazil. Ticks and Tick-Borne Diseases, v. 5, p. 100-104, 2014.

Byrne, K. M., Kim, H. W., Chew, B. P., Reinhart, G. A., Hayek, M. G. A standardized gating technique for the generation of flow cytometry data for normal canine and normal feline blood lymphocytes. Veterinary Immunology and Immunopathology, v. 73, p. 167-182, 2000.

Palmer, G. H., Brown, W. C., Rurangirwa, F. R. Antigenic variation in the persistence and transmission of ehrlichia Anaplasma marginale. Microbes and Infection, v. 2, p. 167-176, 1999.

Eriks, I. S., Palmer, G. H., McGuire, T. C., Allred, D. R., Barbet, A. F. Detection and quantification of Anaplasma marginale in carrier cattle by using a nucleic acid probe. Journal of Clinical Microbiology, v. 27, p. 279-284, 1989.

French, D. M., McElwain, T. F., McGuire, T. C., Palmer, G. H. Expression of Anaplasma marginale major surface protein 2 variants during persistent cyclic rickettsemia. Infection and Immunity, v. 66, p. 1200-1207, 1998.

Brayton, K. A., Meeus, P. F. M., Barbet, A. F., Palmer, G. H. Simultaneous variation of the immunodominant outer membrane proteins, msp2 and msp3, during Anaplasma marginale persistence in vivo. Infection and Immunity, v. 71, p. 6627-6632, 2003.

Futse, J. E., Brayton, K. A., Nydam, S. D., Palmer, G. H. Generation of Antigenic Variants via Gene Conversion: Evidence for recombination fitness selection at the locus level in Anaplasma marginale. Infection and Immunity, v. 77, p. 3181-3187, 2009.

The invention claimed is:

1. A composition comprising at least two hybrid peptides, wherein at least one hybrid peptide comprises two peptide fragments consisting of amino acid sequences SEQ ID NO: 14 and SEQ ID NO: 15 linked together by a spacer element, and wherein at least a second hybrid peptide comprises two peptide fragments consisting of amino acid sequences SEQ ID NO: 13 and SEQ ID NO:19 linked together by a spacer element.

2. The composition of claim 1, wherein the at least one hybrid peptide consists of the amino acid sequence of SEQ ID NO: 23, and the second hybrid peptide consists of the amino acid sequence of SEQ ID NO: 25.

3. The composition of claim 2, comprising at least one additional hybrid peptide, wherein the at least one additional hybrid peptide consists of the amino acid sequence of SEQ ID NO: 20, SEQ ID NO: 21, SEQ ID NO: 22, SEQ ID NO: 24, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33.

4. The composition of claim 3, comprising from 2 to 8 of said additional hybrid peptides.

5. The composition of claim 1, further comprising one or more diluents and/or one or more pharmaceutically acceptable excipients and/or one or more biologically active compounds comprising epitopes capable of inducing an immune response against *Anaplasma marginale* antigens.

6. The composition of claim 1, further comprising one or more adjuvants.

7. The composition of claim 6, said one or more adjuvant being selected from Freund's complete adjuvant, Freund's incomplete adjuvant, aluminum hydroxide, silica and saponin.

8. The composition of claim 1, said composition being in the form of a solution, mixture, powder, granules, aerosol or lyophilized.

9. A method of inducing an immune response, said method comprising administering a therapeutically effective amount of a composition according to claim 1 to a human or animal.

10. The method of claim 9, the therapeutically effective amount being 50 to 150 µg of each hybrid peptide per human or animal.

11. A kit comprising a peptide set, said peptide set comprising at least two of the hybrid peptides of claim 1.

12. The composition of claim 1, each of said spacer elements consisting of 2 to 15 glycine residues.

13. The composition of claim 1, comprising at least one additional hybrid peptide, wherein at least one additional hybrid peptide comprises two peptide fragments consisting of amino acid sequences SEQ ID NO: 5 and SEQ ID NO: 6 linked together by a spacer element.

* * * * *

SEQUENCE LISTING

```
<160> NUMBER OF SEQ ID NOS: 48

<210> SEQ ID NO 1
<211> LENGTH: 20
<212> TYPE: PRT
<213> ORGANISM: Anaplasma marginale

<400> SEQUENCE: 1

Ser Glu Cys Val Ser Leu Gln Pro Thr Asp Ser Ser Ser Ala Ser Gly
1               5                   10                  15

Gln Gln Gln Glu
            20
```

-continued

```
<210> SEQ ID NO 2
<211> LENGTH: 24
<212> TYPE: PRT
<213> ORGANISM: Anaplasma marginale

<400> SEQUENCE: 2

Ala Glu Asp Asp Lys Gln Gln Gln Gln Asn Gln Ser Asn Val Val Gln
1               5                   10                  15

Ala Ile Ser Ala Val Phe Gln Arg
            20

<210> SEQ ID NO 3
<211> LENGTH: 17
<212> TYPE: PRT
<213> ORGANISM: Anaplasma marginale

<400> SEQUENCE: 3

Ser Ser Val Ser Ser Gln Ser Asp Gln Ala Ser Thr Ser Ser Gln Leu
1               5                   10                  15

Gly

<210> SEQ ID NO 4
<211> LENGTH: 14
<212> TYPE: PRT
<213> ORGANISM: Anaplasma marginale

<400> SEQUENCE: 4

Ser Ser Ala Gly Gly Gln Gln Gln Glu Ser Ser Val Ser Ser
1               5                   10

<210> SEQ ID NO 5
<211> LENGTH: 13
<212> TYPE: PRT
<213> ORGANISM: Anaplasma marginale

<400> SEQUENCE: 5

Ser Lys Val Ala Ser Val Glu Tyr Ile Leu Ala Ala Arg
1               5                   10

<210> SEQ ID NO 6
<211> LENGTH: 11
<212> TYPE: PRT
<213> ORGANISM: Anaplasma marginale

<400> SEQUENCE: 6

Gln Val Asp Arg Leu Ala Asn Ala Leu Gly Lys
1               5                   10

<210> SEQ ID NO 7
<211> LENGTH: 21
<212> TYPE: PRT
<213> ORGANISM: Anaplasma marginale

<400> SEQUENCE: 7

Asp Ala Ala Gly Arg Val Asp Phe Lys Val His Asn Phe Asp Trp Ser
1               5                   10                  15

Ala Pro Glu Pro Lys
            20

<210> SEQ ID NO 8
<211> LENGTH: 21
<212> TYPE: PRT
<213> ORGANISM: Anaplasma marginale
```

```
<400> SEQUENCE: 8

Asn Lys Asp Thr Gly Ile Ala Ser Phe Asn Phe Ala Tyr Phe Gly Gly
1               5                   10                  15

Glu Leu Gly Val Arg
            20

<210> SEQ ID NO 9
<211> LENGTH: 23
<212> TYPE: PRT
<213> ORGANISM: Anaplasma marginale

<400> SEQUENCE: 9

Lys Lys Ser Asn Glu Asp Thr Ala Ser Val Phe Leu Leu Gly Lys Glu
1               5                   10                  15

Leu Ala Tyr Asp Thr Ala Arg
            20

<210> SEQ ID NO 10
<211> LENGTH: 24
<212> TYPE: PRT
<213> ORGANISM: Anaplasma marginale

<400> SEQUENCE: 10

Lys Glu Asp Lys Ala Val Val Ala Gly Ala Phe Ala Arg Ala Val Glu
1               5                   10                  15

Gly Ala Glu Val Ile Glu Val Arg
            20

<210> SEQ ID NO 11
<211> LENGTH: 20
<212> TYPE: PRT
<213> ORGANISM: Anaplasma marginale

<400> SEQUENCE: 11

Thr Lys Gly Glu Ala Lys Lys Trp Gly Asn Ala Ile Glu Ser Ala Thr
1               5                   10                  15

Gly Thr Thr Ser
            20

<210> SEQ ID NO 12
<211> LENGTH: 22
<212> TYPE: PRT
<213> ORGANISM: Anaplasma marginale

<400> SEQUENCE: 12

Gly Asp Glu Leu Ser Lys Lys Val Cys Gly Lys Gly Thr Thr Ser Gly
1               5                   10                  15

Ser Thr Asn Gln Cys Gly
            20

<210> SEQ ID NO 13
<211> LENGTH: 17
<212> TYPE: PRT
<213> ORGANISM: Anaplasma marginale

<400> SEQUENCE: 13

Leu Ala Glu Ser Thr Glu Gly Asn Leu Glu Glu Val Trp Ile Leu Gly
1               5                   10                  15

Lys
```

```
<210> SEQ ID NO 14
<211> LENGTH: 20
<212> TYPE: PRT
<213> ORGANISM: Anaplasma marginale

<400> SEQUENCE: 14

Gly Ala Ser Thr Asp Ala Ala Ala Ala Lys Ile Val Ala Met
1               5                   10                  15

Ala Tyr Gly Arg
            20

<210> SEQ ID NO 15
<211> LENGTH: 20
<212> TYPE: PRT
<213> ORGANISM: Anaplasma marginale

<400> SEQUENCE: 15

Gly Ala Ser Ser Val Asp Ala Leu Thr Ala Thr Lys Leu Val Ala Ala
1               5                   10                  15

Ala Leu Gly His
            20

<210> SEQ ID NO 16
<211> LENGTH: 26
<212> TYPE: PRT
<213> ORGANISM: Anaplasma marginale

<400> SEQUENCE: 16

Thr Ile Val Pro Val Lys Thr Phe Asp Asp Gly Ala Leu Thr Tyr Phe
1               5                   10                  15

Gln Phe Tyr Asp Asn Asn Lys Val Ile Pro
            20                  25

<210> SEQ ID NO 17
<211> LENGTH: 21
<212> TYPE: PRT
<213> ORGANISM: Anaplasma marginale

<400> SEQUENCE: 17

Ala Met Gly Asp Ser Val His Trp Lys Val Lys Pro Val Asp Asn Lys
1               5                   10                  15

Leu Phe Ile Met Pro
            20

<210> SEQ ID NO 18
<211> LENGTH: 30
<212> TYPE: PRT
<213> ORGANISM: Anaplasma marginale

<400> SEQUENCE: 18

Leu Gln Gly His Met Ile Asp Ala Val Leu Glu Thr Ala Ile Asn Ser
1               5                   10                  15

Asp Ile Pro Gly Val Leu Arg Ala Ile Val Ser Arg Asp Val
            20                  25                  30

<210> SEQ ID NO 19
<211> LENGTH: 30
<212> TYPE: PRT
<213> ORGANISM: Anaplasma marginale
```

```
<400> SEQUENCE: 19

Phe Ser Glu Ser Met Lys Ala Leu Ile Lys Lys Tyr Val Asp Thr Ser
1               5                   10                  15

Lys Pro Thr Ile Tyr Val Asp Gln Gly Thr Val Met Lys Val
            20                  25                  30

<210> SEQ ID NO 20
<211> LENGTH: 28
<212> TYPE: PRT
<213> ORGANISM: Artificial sequence
<220> FEATURE:
<223> OTHER INFORMATION: Synthetic hybrid peptide

<400> SEQUENCE: 20

Ser Lys Val Ala Ser Val Glu Tyr Ile Leu Ala Ala Arg Gly Gly Gly
1               5                   10                  15

Gly Gln Val Asp Arg Leu Ala Asn Ala Leu Gly Lys
            20                  25

<210> SEQ ID NO 21
<211> LENGTH: 41
<212> TYPE: PRT
<213> ORGANISM: Artificial sequence
<220> FEATURE:
<223> OTHER INFORMATION: Synthetic hybrid peptide

<400> SEQUENCE: 21

Ser Ser Val Ser Ser Gln Ser Asp Gln Ala Ser Thr Ser Ser Gln Leu
1               5                   10                  15

Gly Gly Gly Gly Ala Met Gly Asp Ser Val His Trp Lys Val Lys Pro
            20                  25                  30

Val Asp Asn Lys Leu Phe Ile Met Pro
            35                  40

<210> SEQ ID NO 22
<211> LENGTH: 42
<212> TYPE: PRT
<213> ORGANISM: Artificial sequence
<220> FEATURE:
<223> OTHER INFORMATION: Synthetic hybrid peptide

<400> SEQUENCE: 22

Leu Ala Glu Ser Thr Glu Gly Asn Leu Glu Glu Val Trp Ile Leu Gly
1               5                   10                  15

Lys Gly Gly Gly Gly Asp Glu Leu Ser Lys Lys Val Cys Gly Lys Gly
            20                  25                  30

Thr Thr Ser Gly Ser Thr Asn Gln Cys Gly
            35                  40

<210> SEQ ID NO 23
<211> LENGTH: 44
<212> TYPE: PRT
<213> ORGANISM: Artificial sequence
<220> FEATURE:
<223> OTHER INFORMATION: Synthetic hybrid peptide
```

-continued

```
<400> SEQUENCE: 23

Gly Ala Ser Thr Asp Asp Ala Ala Ala Ala Lys Ile Val Ala Met
1               5                   10                  15

Ala Tyr Gly Arg Gly Gly Gly Gly Ala Ser Ser Val Asp Ala Leu
            20                  25                  30

Thr Ala Thr Lys Leu Val Ala Ala Leu Gly His
            35                  40

<210> SEQ ID NO 24
<211> LENGTH: 50
<212> TYPE: PRT
<213> ORGANISM: Artificial sequence
<220> FEATURE:
<223> OTHER INFORMATION: Synthetic hybrid peptide

<400> SEQUENCE: 24

Gly Ala Ser Thr Asp Asp Ala Ala Ala Ala Lys Ile Val Ala Met
1               5                   10                  15

Ala Tyr Gly Arg Gly Gly Gly Gly Thr Ile Val Pro Val Lys Thr Phe
            20                  25                  30

Asp Asp Gly Ala Leu Thr Tyr Phe Gln Phe Tyr Asp Asn Asn Lys Val
            35                  40                  45

Ile Pro
    50

<210> SEQ ID NO 25
<211> LENGTH: 51
<212> TYPE: PRT
<213> ORGANISM: Artificial sequence
<220> FEATURE:
<223> OTHER INFORMATION: Synthetic hybrid peptide

<400> SEQUENCE: 25

Leu Ala Glu Ser Thr Glu Gly Asn Leu Glu Glu Val Trp Ile Leu Gly
1               5                   10                  15

Lys Gly Gly Gly Gly Phe Ser Glu Ser Met Lys Ala Leu Ile Lys Lys
            20                  25                  30

Tyr Val Asp Thr Ser Lys Pro Thr Ile Tyr Val Asp Gln Gly Thr Val
            35                  40                  45

Met Lys Val
    50

<210> SEQ ID NO 26
<211> LENGTH: 53
<212> TYPE: PRT
<213> ORGANISM: Artificial sequence
<220> FEATURE:
<223> OTHER INFORMATION: Synthetic hybrid peptide

<400> SEQUENCE: 26

Ser Lys Val Ala Ser Val Glu Tyr Ile Leu Ala Ala Arg Gly Gly Gly
1               5                   10                  15

Gly Gln Val Asp Arg Leu Ala Asn Ala Leu Gly Lys Gly Gly Gly Gly
            20                  25                  30

Ala Met Gly Asp Ser Val His Trp Lys Val Lys Pro Val Asp Asn Lys
            35                  40                  45

Leu Phe Ile Met Pro
    50
```

```
<210> SEQ ID NO 27
<211> LENGTH: 54
<212> TYPE: PRT
<213> ORGANISM: Artificial sequence
<220> FEATURE:
<223> OTHER INFORMATION: Synthetic hybrid peptide

<400> SEQUENCE: 27

Ser Glu Cys Val Ser Leu Gln Pro Thr Asp Ser Ser Ala Ser Gly
1               5                   10                  15

Gln Gln Gln Glu Gly Gly Gly Leu Gln Gly His Met Ile Asp Ala
                20                  25                  30

Val Leu Glu Thr Ala Ile Asn Ser Asp Ile Pro Gly Val Leu Arg Ala
            35                  40                  45

Ile Val Ser Arg Asp Val
    50

<210> SEQ ID NO 28
<211> LENGTH: 48
<212> TYPE: PRT
<213> ORGANISM: Artificial sequence
<220> FEATURE:
<223> OTHER INFORMATION: Synthetic hybrid peptide

<400> SEQUENCE: 28

Ser Ser Ala Gly Gly Gln Gln Gln Glu Ser Ser Val Ser Ser Gly Gly
1               5                   10                  15

Gly Gly Leu Gln Gly His Met Ile Asp Ala Val Leu Glu Thr Ala Ile
                20                  25                  30

Asn Ser Asp Ile Pro Gly Val Leu Arg Ala Ile Val Ser Arg Asp Val
            35                  40                  45

<210> SEQ ID NO 29
<211> LENGTH: 73
<212> TYPE: PRT
<213> ORGANISM: Artificial sequence
<220> FEATURE:
<223> OTHER INFORMATION: Synthetic hybrid peptide

<400> SEQUENCE: 29

Ala Glu Asp Asp Lys Gln Gln Gln Gln Asn Gln Ser Asn Val Val Gln
1               5                   10                  15

Ala Ile Ser Ala Val Phe Gln Arg Gly Gly Gly Gly Ala Ser Thr
                20                  25                  30

Asp Asp Ala Ala Ala Ala Lys Ile Val Ala Met Ala Tyr Gly Arg
            35                  40                  45

Gly Gly Gly Gly Ala Met Gly Asp Ser Val His Trp Lys Val Lys Pro
        50                  55                  60

Val Asp Asn Lys Leu Phe Ile Met Pro
65                  70

<210> SEQ ID NO 30
<211> LENGTH: 55
<212> TYPE: PRT
<213> ORGANISM: Artificial sequence
<220> FEATURE:
<223> OTHER INFORMATION: Synthetic hybrid peptide
```

```
<400> SEQUENCE: 30

Asp Ala Ala Gly Arg Val Asp Phe Lys Val His Asn Phe Asp Trp Ser
1               5                   10                  15

Ala Pro Glu Pro Lys Gly Gly Gly Leu Gln Gly His Met Ile Asp
            20                  25                  30

Ala Val Leu Glu Thr Ala Ile Asn Ser Asp Ile Pro Gly Val Leu Arg
            35                  40                  45

Ala Ile Val Ser Arg Asp Val
        50                  55

<210> SEQ ID NO 31
<211> LENGTH: 52
<212> TYPE: PRT
<213> ORGANISM: Artificial sequence
<220> FEATURE:
<223> OTHER INFORMATION: Synthetic hybrid peptide

<400> SEQUENCE: 31

Asn Lys Asp Thr Gly Ile Ala Ser Phe Asn Phe Ala Tyr Phe Gly Gly
1               5                   10                  15

Glu Leu Gly Val Arg Gly Gly Gly Gly Thr Ile Val Pro Val Lys
            20                  25                  30

Thr Phe Asp Asp Gly Ala Leu Thr Tyr Phe Gln Phe Tyr Asp Asn Asn
            35                  40                  45

Lys Val Ile Pro
        50

<210> SEQ ID NO 32
<211> LENGTH: 57
<212> TYPE: PRT
<213> ORGANISM: Artificial sequence
<220> FEATURE:
<223> OTHER INFORMATION: Synthetic hybrid peptide

<400> SEQUENCE: 32

Lys Lys Ser Asn Glu Asp Thr Ala Ser Val Phe Leu Leu Gly Lys Glu
1               5                   10                  15

Leu Ala Tyr Asp Thr Ala Arg Gly Gly Gly Gly Leu Gln Gly His Met
            20                  25                  30

Ile Asp Ala Val Leu Glu Thr Ala Ile Asn Ser Asp Ile Pro Gly Val
            35                  40                  45

Leu Arg Ala Ile Val Ser Arg Asp Val
        50                  55

<210> SEQ ID NO 33
<211> LENGTH: 68
<212> TYPE: PRT
<213> ORGANISM: Artificial sequence
<220> FEATURE:
<223> OTHER INFORMATION: Synthetic hybrid peptide

<400> SEQUENCE: 33

Thr Lys Gly Glu Ala Lys Lys Trp Gly Asn Ala Ile Glu Ser Ala Thr
1               5                   10                  15

Gly Thr Thr Ser Gly Gly Gly Gly Ser Glu Cys Val Ser Leu Gln Pro
            20                  25                  30

Thr Asp Ser Ser Ser Ala Ser Gly Gln Gln Gln Glu Gly Gly Gly Gly
            35                  40                  45
```

Gly Ala Ser Ser Val Asp Ala Leu Thr Ala Thr Lys Leu Val Ala Ala
            50                  55                  60

Ala Leu Gly His
 65

<210> SEQ ID NO 34
<211> LENGTH: 20
<212> TYPE: DNA
<213> ORGANISM: Artificial sequence
<220> FEATURE:
<223> OTHER INFORMATION: forward primer

<400> SEQUENCE: 34
ttttacgtgc ccaaggttaa                                           20

<210> SEQ ID NO 35
<211> LENGTH: 20
<212> TYPE: DNA
<213> ORGANISM: Artificial sequence
<220> FEATURE:
<223> OTHER INFORMATION: reverse primer

<400> SEQUENCE: 35
cgtttactgt tgcatcatca                                           20

<210> SEQ ID NO 36
<211> LENGTH: 20
<212> TYPE: DNA
<213> ORGANISM: Artificial sequence
<220> FEATURE:
<223> OTHER INFORMATION: forward primer

<400> SEQUENCE: 36
ataaccaggt cattcaaagg                                           20

<210> SEQ ID NO 37
<211> LENGTH: 20
<212> TYPE: DNA
<213> ORGANISM: Artificial sequence
<220> FEATURE:
<223> OTHER INFORMATION: reverse primer

<400> SEQUENCE: 37
attctgactt ctcttccgct                                           20

<210> SEQ ID NO 38
<211> LENGTH: 19
<212> TYPE: DNA
<213> ORGANISM: Artificial sequence
<220> FEATURE:
<223> OTHER INFORMATION: forward primer

<400> SEQUENCE: 38
ccagagggaa gagcagtcc                                            19

<210> SEQ ID NO 39
<211> LENGTH: 19
<212> TYPE: DNA
<213> ORGANISM: Artificial sequence
<220> FEATURE:
<223> OTHER INFORMATION: reverse primer

<400> SEQUENCE: 39
ggctacaacg tgggctacc                                            19

-continued

```
<210> SEQ ID NO 40
<211> LENGTH: 20
<212> TYPE: DNA
<213> ORGANISM: Artificial sequence
<220> FEATURE:
<223> OTHER INFORMATION: forward primer

<400> SEQUENCE: 40
aacctgcaac tgagaccatt                                               20

<210> SEQ ID NO 41
<211> LENGTH: 20
<212> TYPE: DNA
<213> ORGANISM: Artificial sequence
<220> FEATURE:
<223> OTHER INFORMATION: reverse primer

<400> SEQUENCE: 41
atccttgtgg catgtgactt                                               20

<210> SEQ ID NO 42
<211> LENGTH: 19
<212> TYPE: DNA
<213> ORGANISM: Artificial sequence
<220> FEATURE:
<223> OTHER INFORMATION: forward primer

<400> SEQUENCE: 42
tgctggatga ctttaaggg                                                19

<210> SEQ ID NO 43
<211> LENGTH: 19
<212> TYPE: DNA
<213> ORGANISM: Artificial sequence
<220> FEATURE:
<223> OTHER INFORMATION: reverse primer

<400> SEQUENCE: 43
agggcagaaa gcgatgaca                                                19

<210> SEQ ID NO 44
<211> LENGTH: 21
<212> TYPE: DNA
<213> ORGANISM: Artificial sequence
<220> FEATURE:
<223> OTHER INFORMATION: forward primer

<400> SEQUENCE: 44
gaggtctcta taccatggct c                                             21

<210> SEQ ID NO 45
<211> LENGTH: 20
<212> TYPE: DNA
<213> ORGANISM: Artificial sequence
<220> FEATURE:
<223> OTHER INFORMATION: reverse primer

<400> SEQUENCE: 45
gtaccaggcc tgtaacgatg                                               20

<210> SEQ ID NO 46
<211> LENGTH: 18
<212> TYPE: DNA
<213> ORGANISM: Artificial sequence
<220> FEATURE:
<223> OTHER INFORMATION: forward primer
```

```
<400> SEQUENCE: 46
ttggcaaggc agcagctt                                                      18

<210> SEQ ID NO 47
<211> LENGTH: 18
<212> TYPE: DNA
<213> ORGANISM: Artificial sequence
<220> FEATURE:
<223> OTHER INFORMATION: reverse primer

<400> SEQUENCE: 47
ttccgcgagc atgtgcat                                                      18

<210> SEQ ID NO 48
<211> LENGTH: 26
<212> TYPE: DNA
<213> ORGANISM: Artificial sequence
<220> FEATURE:
<223> OTHER INFORMATION: PCR probe

<400> SEQUENCE: 48
tcggtctaac atctccaggc tttcat                                             26
```